(12) United States Patent
Zhang et al.

(10) Patent No.: US 12,005,148 B2
(45) Date of Patent: Jun. 11, 2024

(54) COOLANT-COOLED HEAT SINK(S) WITH ASSOCIATED ULTRA-VIOLET LIGHT ASSEMBLY

(71) Applicant: INTERNATIONAL BUSINESS MACHINES CORPORATION, Armonk, NY (US)

(72) Inventors: Hongqing Zhang, Hopewell Junction, NY (US); David J. Lewison, LaGrangeville, NY (US); Frank L. Pompeo, Redding, CT (US); James Busby, New Paltz, NY (US); Jay A. Bunt, Esopus, NY (US); Joyce E. Molinelli Acocella, Poughquag, NY (US); Madhana Sunder, Poughkeepsie, NY (US); Michael J. Ellsworth, Jr., LaGrangeville, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 609 days.

(21) Appl. No.: 17/245,356

(22) Filed: Apr. 30, 2021

(65) Prior Publication Data
US 2022/0347327 A1 Nov. 3, 2022

(51) Int. Cl.
*A61L 2/10* (2006.01)
*F21V 29/58* (2015.01)
*H05K 7/20* (2006.01)

(52) U.S. Cl.
CPC ............. *A61L 2/10* (2013.01); *F21V 29/59* (2015.01); *A61L 2202/11* (2013.01); *A61L 2202/14* (2013.01); *H05K 7/20763* (2013.01)

(58) Field of Classification Search
CPC .. H05K 7/20; H05K 7/20709; H05K 7/20763; H05K 7/20772; A61L 2202/11
See application file for complete search history.

(56) References Cited

U.S. PATENT DOCUMENTS

| 5,114,576 A | 5/1992 | Ditzler et al. |
| 5,547,590 A | 8/1996 | Szabo |
| 6,404,111 B1 | 6/2002 | Kunkel |

(Continued)

FOREIGN PATENT DOCUMENTS

| CN | 101132681 A | 2/2008 |
| CN | 103612498 A | 3/2014 |

(Continued)

OTHER PUBLICATIONS

International Search Report & Written Opinion for PCT/IB2022/053511, dated Jul. 20, 2022 (8 pages) (Year: 2022).

*Primary Examiner* — Sean E Conley
*Assistant Examiner* — Justin Hwang
(74) *Attorney, Agent, or Firm* — Tihon Poltavets, Esq; Kevin P. Radigan, Esq.; Heslin Rothenberg Farley & Mesiti P.C.

(57) ABSTRACT

Apparatuses and methods of fabrication are provided which include a coolant-cooled heat sink through which coolant passes to facilitate cooling the coolant-cooled heat sink, and an ultra-violet (UV) light assembly associated with the coolant-cooled heat sink for directing UV light towards an interior surface of the coolant-cooled heat sink across which the coolant passes. The UV light inhibits bacterial growth at the interior surface of the coolant-cooled heat sink.

17 Claims, 19 Drawing Sheets

(56) References Cited

U.S. PATENT DOCUMENTS

| | | |
|---|---|---|
| 6,779,739 B2 | 8/2004 | Mulvaney |
| 7,669,530 B2 | 3/2010 | Aylor et al. |
| 8,226,831 B2 | 7/2012 | Maiden |
| 8,506,886 B2 | 8/2013 | Owen et al. |
| 9,366,013 B2 | 6/2016 | Rife et al. |
| 9,855,350 B1 | 1/2018 | Dahlquist |
| 10,330,304 B2 | 6/2019 | Johnson, III et al. |
| 2012/0273340 A1* | 11/2012 | Felix .................... B01D 53/007 204/157.3 |
| 2016/0143184 A1 | 5/2016 | Campbell et al. |
| 2018/0370822 A1* | 12/2018 | Watanabe ............... C02F 1/325 |
| 2019/0142986 A1* | 5/2019 | Zhang .................... C02F 1/325 250/436 |

FOREIGN PATENT DOCUMENTS

| | | |
|---|---|---|
| CN | 204076443 U | 1/2015 |
| CN | 207857307 U | 9/2018 |
| DE | 2020-04007119 U1 | 8/2004 |
| DE | 2020-04017044 U1 | 2/2005 |
| DE | 2020-11102997 U1 | 12/2011 |
| JP | 2004-354471 A | 12/2004 |
| JP | 2006-322658 A | 11/2006 |
| JP | 2014-082311 A | 5/2015 |
| JP | 2016-203095 A | 12/2016 |
| JP | 2016203095 A * | 12/2016 |
| JP | 2019-530232 A | 10/2019 |
| KR | 101464355 B1 | 11/2014 |
| KR | 10-20190040024 A | 4/2019 |

\* cited by examiner

FIG. 1

COOLANT-COOLED HEAT SINK(S) WITH ASSOCIATED ULTRA-VIOLET LIGHT ASSEMBLY

BACKGROUND

Operating electronic components produce heat, which needs to be removed in an effective manner in order to maintain device junction temperatures within desirable limits, with failure to do so resulting in excessive component temperatures, potentially leading to thermal runaway conditions. Several trends in the electronics industry combine to increase the importance of thermal management, including in technologies where thermal management has traditionally been less of a concern. In particular, the need for faster and more densely packed circuits has had a direct impact on the importance of thermal management. For instance, power dissipation, and therefore heat production, increases as device operating frequencies increase. Also, increased operating frequencies are possible at lower device junction temperatures. Further, as more and more components are packed onto a single chip, heat flux (Watts/cm$^2$) increases, resulting in the need to dissipate more power from a given sized chip, module, or system. These trends have combined to create applications where traditional air-cooling methods alone, such as methods using air-cooled heat sinks with heat pipes or vapor chambers, are unable to remove sufficient heat.

The need to cool current and future high-heat load, high-heat flux electronic components thus mandates the continued development of more aggressive thermal management techniques using, for instance, liquid-cooling. Various types of liquid coolants and liquid-cooling approaches are known, and provide different cooling capabilities. For instance, fluids such as refrigerants or other dielectric liquids (e.g., fluorocarbon liquids) exhibit lower thermal conductivity and specific heat properties, compared to liquids such as water or other aqueous fluids, but can be placed in direct physical contact with electronic components and their associated interconnects without adverse effects, such as corrosion or electrical short circuits. Other coolant liquids, such as water or other aqueous fluids, exhibit superior thermal conductivity and specific heat compared to dielectric fluids. However, water-based coolants must be separated from physical contact with the electronic components and interconnects, since corrosion and electrical short circuit problems are otherwise likely to result. This is typically accomplished by flowing the liquid coolant through a liquid-cooled heat sink or cold plate.

SUMMARY

Certain shortcomings of the prior art are overcome, and additional advantages are provided through the provision of an apparatus which includes a coolant-cooled heat sink through which coolant passes to facilitate cooling the coolant-cooled heat sink, and an ultra-violet (UV) light assembly associated with the coolant-cooled heat sink for directing UV light towards an interior surface of the coolant-cooled heat sink. The UV light source is directed towards the interior surface of the coolant-cooled heat sink to inhibit bacterial growth at the interior surface of the coolant-cooled heat sink.

In another aspect, an apparatus is provided which includes multiple coolant-cooled heat sinks through which coolant passes to facilitate cooling the multiple coolant-cooled heat sinks, and an ultra-violet (UV) light assembly associated with the multiple coolant-cooled heat sinks for directing UV light towards respective interior surfaces of the multiple coolant-cooled heat sinks across which the coolant passes. The UV light inhibits bacterial growth at the respective interior surfaces of the multiple coolant-cooled heat sinks.

In a further aspect, a method is provided which includes: providing a coolant-cooled heat sink through which coolant passes to facilitate cooling the coolant-cooled heat sink; and associating an ultra-violet (UV) light assembly with the coolant-cooled heat sink for directing UV light towards an interior surface of the coolant-cooled heat sink across which the coolant passes. The UV light inhibits bacterial growth at the interior surface of the coolant-cooled heat sink.

Additional features and advantages are realized through the techniques of the present invention. Other embodiments and aspects of the invention are described in detail herein and are considered a part of the claimed invention.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

FIG. 1 depicts one embodiment of a coolant-cooled data center with a coolant distribution unit facilitating liquid-cooling of electronic systems within racks of the data center, with one or more electronic systems including one or more apparatuses in accordance with one or more aspects of the present invention;

DETAILED DESCRIPTION

Figure 2A:
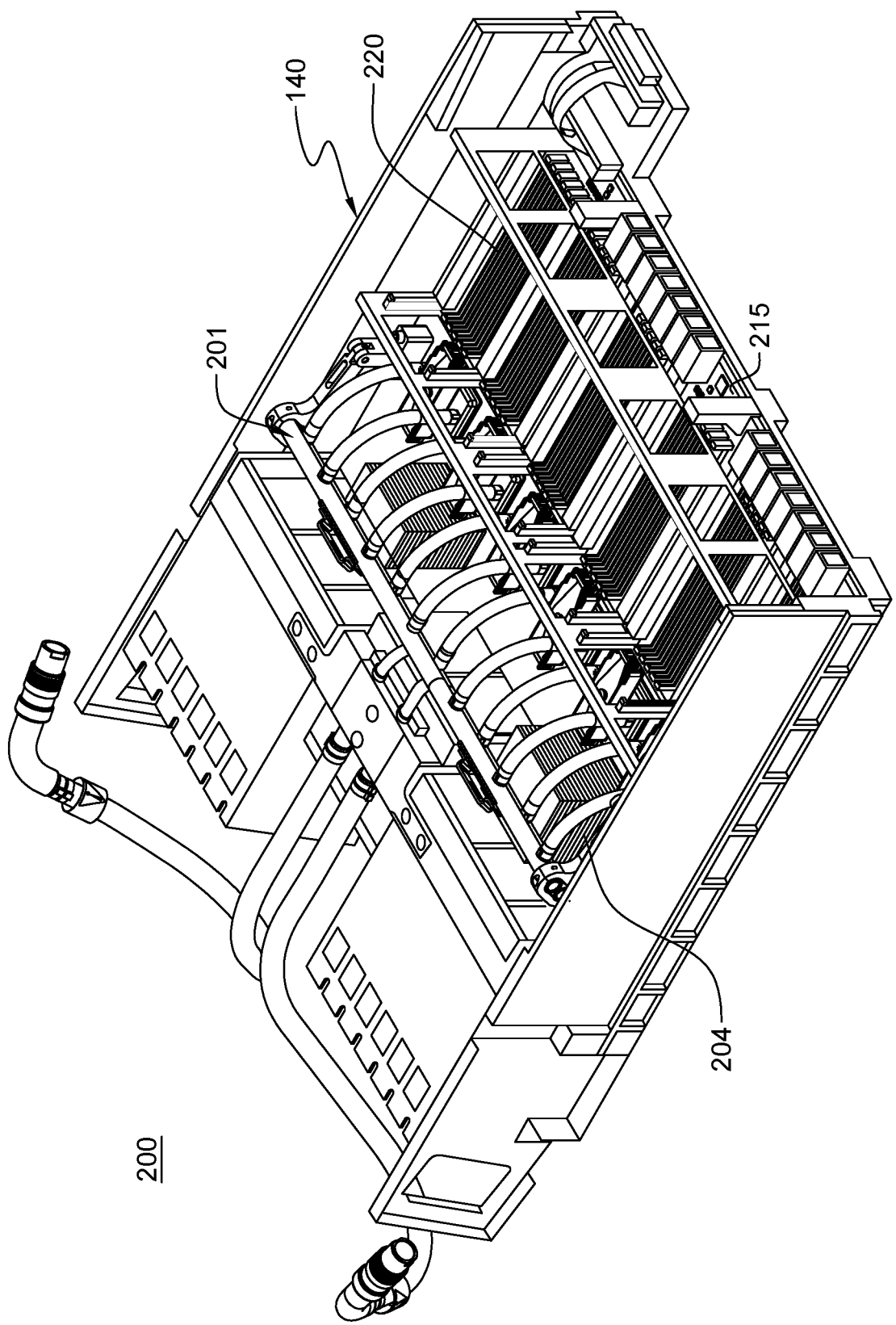
FIG. 2A depicts one embodiment of a partially assembled electronic system and cooling assembly layout, wherein the electronic system includes, by way of example, multiple heat-generating electronic components to be actively cooled by the cooling assembly, and to include one or more apparatuses in accordance with one or more aspects of the present invention.

Aspects of the present invention and certain features, advantages and details thereof, are explained more fully below with reference to the non-limiting example(s) illustrated in the accompanying drawings. Descriptions of well-known materials, systems, devices, fabricating techniques, processes, etc., are omitted so as to not unnecessarily obscure the invention in detail. It should be understood, however, that the detailed description in this specific example(s), while indicating aspects of the invention, is given by way of illustration only, and not by way of limitation. Various substitutions, modifications, additions, and/or other arrangements, within the spirit and/or scope of the underlying inventive concepts will be apparent to those skilled in the art from this disclosure. Note further that numerous inventive aspects and features are disclosed herein, and unless inconsistent, each disclosed aspect or feature is combinable with any other disclosed aspect or feature as desired for a particular application of the concepts disclosed herein.

An electronics rack, or IT rack, can include any housing, frame, rack, compartment, blade server system, etc., containing or having (for instance) one or more heat-generating components of a computer system, electronic system, information technology equipment, etc. In one or more embodiments, an electronics rack can include a portion of an electronic system, a single electronic system, or multiple electronic systems, for instance, in one or more sub-housings, blades, books, drawers, nodes, compartments, etc., each having one or more heat-generating electronic components disposed therein. An electronic system within an electronics rack can be movable or fixed relative to the electronics rack, with rack-mounted electronic drawers being an example of systems of an electronics rack to be cooled.

An electronic component can refer to any heat-generating electronics component of, for instance, a computer system or other electronics unit requiring cooling. By way of example, an electronic component can include one or more integrated circuit die (or chips), and/or other electronic devices to be cooled, including one or more processor chips, such as central processing unit (CPU) chips and/or graphics processing unit (GPU) devices. Further, the term coolant-cooled heat sink or cold plate refers, in one embodiment, to a thermally-conductive structure or assembly having one or more internal compartments, channels, passageways, etc., formed therein for flowing of coolant therethrough.

One example of coolant to be used within a coolant-cooled heat sink discussed herein is water or an aqueous-based solution which includes an anti-corrosion material or corrosion inhibitor, such as Benzotriazole (BTA). However, the cooling concepts disclosed herein are readily adapted to use with other types of coolant.

Figure 1:
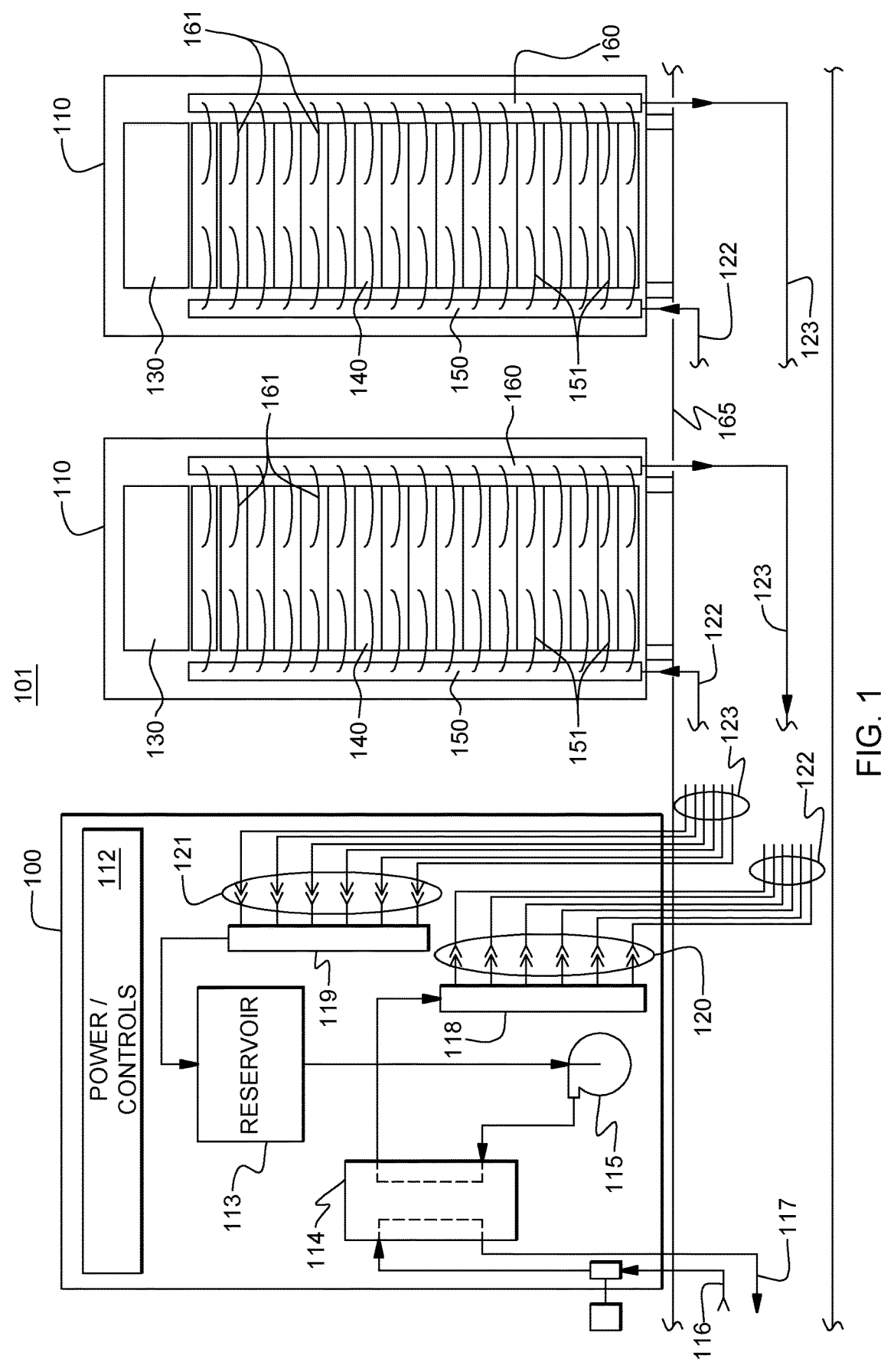

As noted, due to the ever-increasing airflow requirements through electronics racks of a data center, and the limits of air distribution within a typical data center installation, it can be desirable for liquid-based cooling to, for instance, be combined with, or used in place of, conventional air-cooling. By way of example only, FIGS. 1-3 illustrate one embodiment of a data center and electronics system employing a liquid-based cooling system or cooling assembly with one or more coolant-cooled heat sinks coupled to high-heat-generating electronic components disposed within one or more electronic systems of one or more electronics racks.

In particular, FIG. 1 depicts one embodiment of a data center 101 including a coolant distribution unit 100. The coolant distribution unit can be a relatively large unit which occupies what would be considered a full electronics frame. Within coolant distribution unit 100 is a power/control element 112, a reservoir/expansion tank 113, a heat exchanger 114, a pump 115 (possibly accompanied by a redundant second pump), facility water inlet 116 and outlet 117 supply pipes, a supply manifold 118 supplying water or system coolant to the electronics racks 110 via couplings 120 and lines 122, and a return manifold 119 receiving water from the electronics racks 110, via lines 123 and couplings 121. Each electronics rack includes (in one example) a power/control unit 130 for the electronics rack, multiple electronic systems 140, a system coolant supply manifold 150, and a system coolant return manifold 160. By way of example only, electronics rack 110 are disposed on a raised floor 165 of data center 101, with lines 122 providing system coolant to system coolant supply manifolds 150 and lines 123 facilitating return of system coolant from system coolant return manifolds 160 being disposed beneath the raised floor.

In one embodiment, system coolant supply manifold 150 provides system coolant to the cooling assemblies of the electronic systems (including to coolant-cooled heat sinks thereof) via flexible hose connections 151, which are disposed between the supply manifold and the respective electronic systems within the rack. Similarly, system coolant return manifold 160 is coupled to the electronic systems via flexible hose connections 161. Quick connect couplings can be employed at the interface between flexible hoses 151, 161 and the individual electronic systems.

Figure 2B:
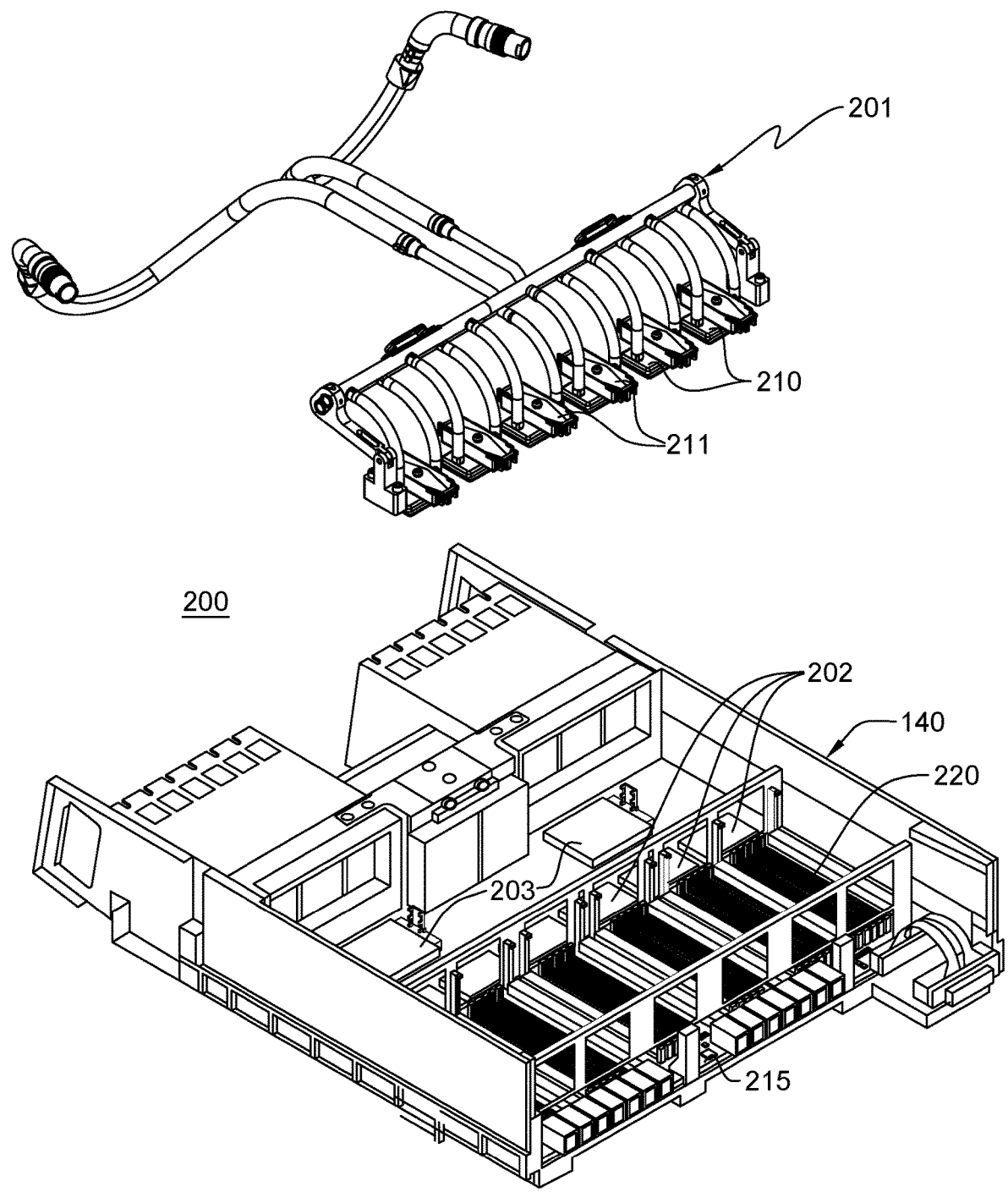
FIG. 2B depicts the electronic system and cooling assembly layout of FIG. 2A, with the cooling assembly shown exploded from the electronic system, in accordance with one or more aspects of the present invention.
Figure 3:
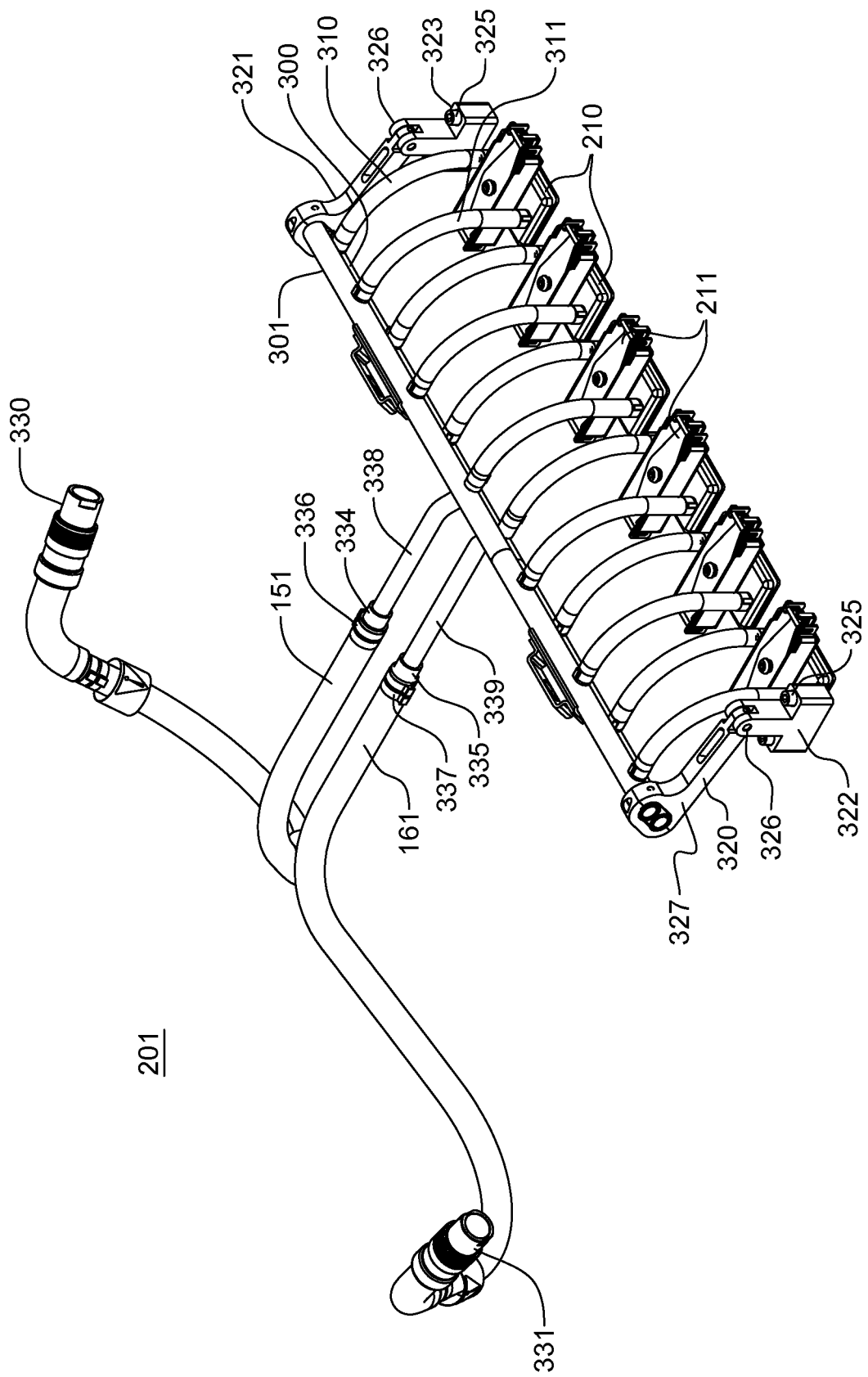
FIG. 3 is an enlarged view of the cooling assembly of FIGS. 2A & 2B, in accordance with one or more aspects of the present invention.

FIGS. 2A & 2B depict one embodiment of a cooled electronic system 200, in accordance with one or more aspects of the present invention. By way of example, cooled electronic system 200 includes electronic system 140, such as the above-described drawer- or node-level electronic system of FIG. 1, and a flexible coolant manifold-heat sink assembly 201 coupled thereto, in accordance with one or more aspects of the present invention. In this implementation, flexible coolant manifold-heat sink assembly 201 is a drawer- or node-level cooling assembly with multiple coolant-cooled heat sinks 210, each configured and sized to attach to and cool a respective electronic component 202, such as a respective high-heat-generating electronic component of a server node. In one example, respective loading brackets 211 can be provided to facilitate secure attachment and loading of coolant-cooled heat sinks 210 to electronic components 202 to ensure good thermal conduction from electronic components 202 to coolant-cooled heat sinks 210.

As one detailed example, the exemplary electronic system of FIGS. 2A & 2B can be an electronics drawer or planar server assembly, which includes a multilayer printed circuit board to which memory sockets and various electronic components to be cooled are attached, both physically and electrically. As illustrated, electronic system 140 can include a support substrate or planar board 215, a plurality of memory module sockets 220 (e.g., dual in-line memory module sockets), as well as high-heat-generating processor modules 202, and other components 203, such as memory support modules, which produce less heat and can be air-cooled.

By way of example only, in one or more implementations, one or more other components 203 of electronic system 140 can be air-cooled by an airflow established using one or more air-moving devices (not shown) within electronic system 140, or the electronics rack housing the system. As illustrated, the one or more other components 203 to be air-cooled may have one or more air-cooled heat sinks 204 (FIG. 2A) physically coupled thereto. Note that in the particular embodiment depicted, flexible coolant manifold-heat sink assembly 201 includes a pivotable coolant supply manifold and pivotable coolant return manifold disposed in a first, operational position in FIG. 2A, laterally offset from the row of coolant-cooled heat sinks 210, but overlying the one or more other components 203 of electronic system 140, such as one or more single-chip modules to which air-cooled heat sinks 204 are coupled.

FIG. 3 depicts an enlarged view of one embodiment of flexible coolant manifold-heat sink assembly 201. Note that this implementation of cooling assembly 201 is a drawer- or node-level implementation designed to reside within an electronic system chassis of, for instance, one or more electronic system chassis within an electronics rack, and is discussed herein by way of example only. As illustrated, in addition to multiple coolant-cooled heat sinks 210, flexible coolant manifold-heat sink assembly 201 includes a pivotable coolant supply manifold 300 and a pivotable coolant return manifold 301, which are coupled in this embodiment at opposite ends to a first pivot arm 320 and a second pivot arm 321. Flexible coolant supply conduits 310 and flexible coolant return conduits 311 couple, in the illustrated example, each coolant-cooled heat sink 210 in fluid communication with pivotable coolant supply manifold 300 and pivotable coolant return manifold 301 to allow for flow of coolant, such as liquid coolant, through the heat sinks to facilitate extraction of heat generated by the associated electronic components to which the heat sinks are coupled. Note that, by way of example, each coolant-cooled heat sink 210 has a flexible coolant supply conduit 310 and a flexible coolant return conduit 311 coupled thereto for direct supply and return of coolant through the coolant-cooled heat sink. Thus, in the illustrated embodiment, coolant, such as liquid coolant, flows in parallel through the heat sinks between the pivotable coolant supply manifold 300 and pivotable coolant return manifold 301.

As noted, respective loading brackets 211 can be provided to facilitate (in part) a good thermal interface and good thermal conduction between coolant-cooled heat sinks 210 and the associated electronic components 202 (FIG. 2B) to be cooled. Flexible coolant supply conduits 310 and flexible coolant return conduits 311 are, in one embodiment, fabricated of a flexible, insulative material, such as rubber, and are of sufficient length to couple rigid coolant-cooled heat sinks 210 to pivotable coolant supply manifold 300 and pivotable coolant return manifold 301, via appropriate hose barb fittings and hose clamps. Note that the length of each coolant supply conduit 310 and coolant return conduit 311 is also sufficient to allow for pivotable movement of the rigid pivotable coolant supply manifold 300 and rigid pivotable coolant return manifold 301 between a first position, illustrated in FIG. 3, and a second service position, not illustrated. Note in this regard that the first and second pivot arms 320, 321 include respective base members 322, 323 which facilitate fastening of the first and second pivot arms to, for instance, a structure associated with the electronic system including the electronic components to be cooled. For instance, the first and second pivot arms 320, 321 could be affixed using mechanical fasteners 325 to the support substrate or planar system board in the example of FIGS. 2A & 2B. Note also, in the example depicted in FIG. 3, first and second pivot arms 320, 321 align with the row of coolant-cooled heat sinks 210, and include a pivot axis 326 at upper ends of base members 322, 323, about which pivot elements 327 of the first and second pivot arms 320, 321, pivot. In the example depicted, the pivot axis 326 is at an elevated height above the row of coolant-cooled heat sinks 210, and pivotable coolant supply manifold 300 and pivotable coolant return manifold 301 are at an elevation higher than the coolant-cooled heat sinks when installed within the associated electronic system.

Flexibility is further achieved in the cooling assembly disclosed using flexible manifold-to-node fluid connect hoses 151, 161 to connect flexible coolant manifold-heat sink assembly 201 to, for instance, rack-level coolant supply and return manifolds, respectively (see FIGS. 1-2B). In one or more implementations, respective quick connect couplings 330, 331 at the ends of flexible manifold-to-node fluid connect hoses 151, 161, can be provided, and rigid tube extensions 338, 339 can respectively extend from pivotable coolant supply manifold 300 and pivotable coolant return manifold 301 and facilitate coupling of flexible manifold-to-node fluid connect hoses 151, 161 to the corresponding pivotable coolant supply and return manifolds using, for instance, respective hose barb fittings 334, 335 and hose clamps 336, 337. Note that, in one implementation, pivoting of pivotable coolant supply and return manifolds 300, 301 can be facilitated by providing flexible manifold-to-node fluid connect hoses 151,161 with sufficient length to allow for transition of the pivotable coolant supply and return manifolds 300, 301 between their respective first and second positions, as described. Alternatively, the respective quick connect couplings 330, 331 with poppets can be disengaged from, for instance, the rack-level coolant supply and return manifolds (FIG. 1) prior to pivoting of the pivotable coolant supply and return manifolds 300, 301 from the illustrated first position to their second position.

Figure 7A:
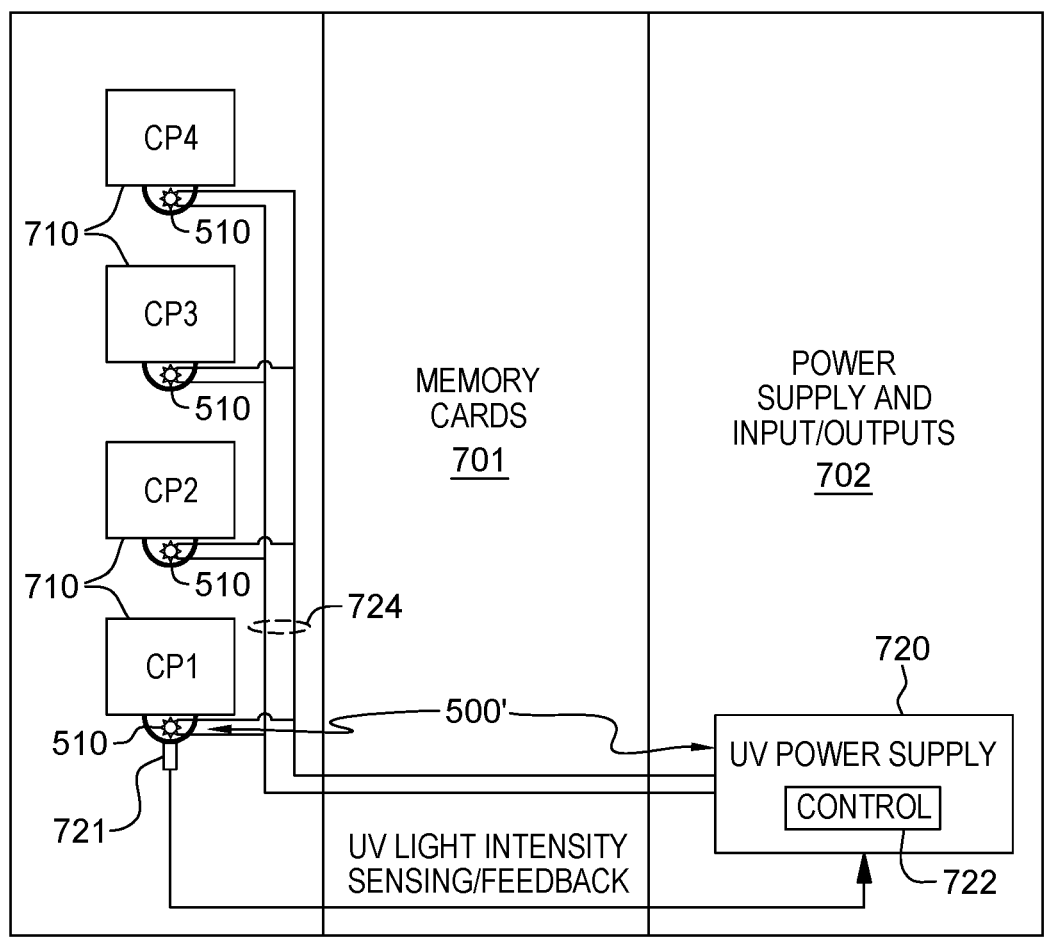
FIG. 7A is a block diagram of one embodiment of an apparatus including multiple coolant-cooled heat sinks (such as disclosed herein) with an associated ultra-violet (UV) light assembly, in accordance with one or more aspects of the present invention.
Figure 8:
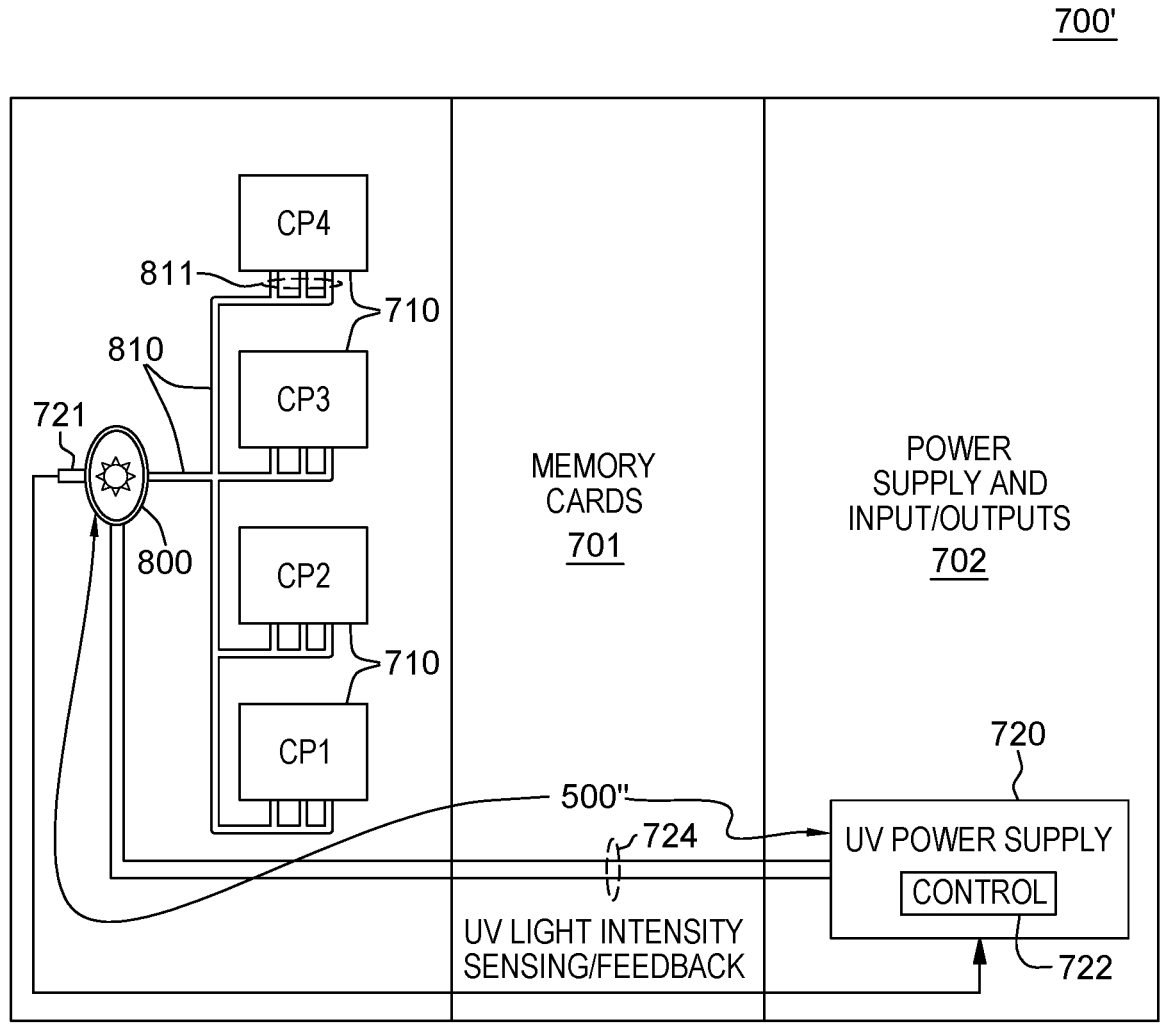
FIG. 8 is a block diagram of another embodiment of an apparatus including multiple coolant-cooled heat sinks and an associated ultra-violet (UV) light assembly, in accordance with one or more aspects of the present invention.

By way of example, and as illustrated in FIGS. 2A & 3, pivotable coolant supply and return manifolds 300, 301 can be in a first position to, for instance, facilitate inclusion of the cooling assembly within the electronic system housing, drawer, chassis, etc., and operational insertion of the resultant cooled electronic system within the respective electronics rack. From this position, flexible coolant supply and return conduits 310, 311, and (in one or more embodiments) flexible manifold-to-node fluid connect hoses 151, 161 allow for pivoting of pivotable coolant supply and return manifolds 300, 301 to a second position, such as for servicing. Note that the in-line, six electronic component and coolant-cooled heat sink example of FIGS. 2A-3, and the in-line, four coolant-cooled heat sink examples of FIGS. 7A & 8, are provided by way of example only. In general, the coolant-cooled heat sinks disclosed herein can be used in a wide variety of coolant-based cooling systems to facilitate active cooling of one or more heat-generating components, such as one or more heat-generating electronic components of an electronic system, such as described above in connection with FIGS. 1-3, by way of example.

In one or more embodiments, the coolant-cooled heat sink(s) of a cooling system can be partially or completely formed of a thermally-conductive metal material, such as copper or a copper alloy. Further, in one or more implementations, high-heat flux removal is facilitated by forming an array of thermally-conductive fins, such as an array of finely spaced, copper fins, extending interior to a coolant-carrying compartment of a closed coolant loop heat sink structure. In one embodiment, high-temperature brazing processes can be used to form hermetic (coolant-tight) seals between the cover plate, thermally-conductive fins, heat transfer base plate and coolant inlet and outlet hose barb connections.

By way of example, the plurality of thermally-conductive fins within the heat sink can include a plurality of parallel-disposed thermally-conductive plate fins, which define channels between the fins, into which coolant is introduced and flows, for example, from an inlet side of the coolant-cooled heat sink to an outlet side of the coolant-cooled heat sink, in a direction substantially parallel to the main heat transfer surface of the heat transfer base. Those skilled in the art should note, however, that the concepts disclosed herein can be used in association with differently configured thermally-conductive fins extending into the coolant-carrying channel from the heat transfer base. For instance, in one or more other embodiments, the thermally-conductive fins can include a plurality of thermally-conductive pin fins extending into the coolant-carrying compartment from the surface of the heat transfer base opposite to the heat transfer surface.

FIGS. 4A-4D depict one embodiment of an apparatus 400, which includes a coolant-cooled heat sink with a plurality of thermally-conductive fins. As illustrated, apparatus 400 is coupled to one or more electronic components 401 (FIG. 4A) and includes a coolant-cooled heat sink 410 (shown in exploded view in FIG. 4A). The one or more electronic components 401 can be disposed, for instance, on a supporting substrate 402, which can facilitate electrical connection of the electronic component(s) to other component(s) of an electronic system, such as described above.

Figure 4A:
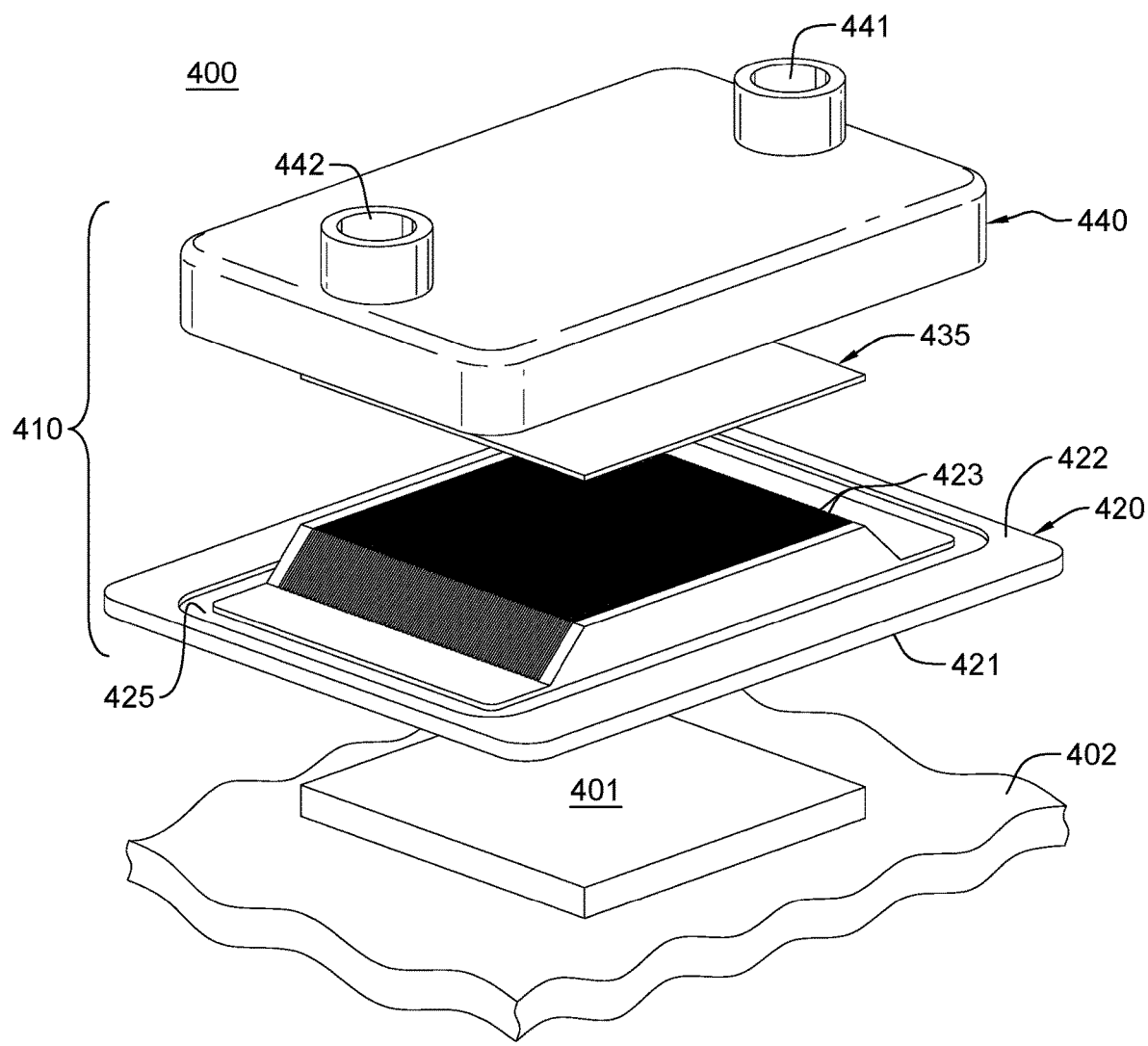
FIG. 4A depicts an exploded view of one embodiment an apparatus including one or more electronic components to be cooled, and a coolant-cooled heat sink for a cooling assembly, such as (for instance) the cooling assembly embodiment of FIGS. 1-3, and which can include an ultra-violet (UV) light assembly, in accordance with one or more aspects of the present invention.

Referring to FIG. 4A, coolant-cooled heat sink 410 includes, for instance, a thermal transfer base 420, a joining material 435, and a cover 440. In the depicted embodiment, heat transfer base 420, which is an active cooling portion, or heat transfer portion, of the coolant-cooled heat sink, is rectangular-shaped, by way of example only. In one or more embodiments, heat transfer base 420 is thermally-conductive, being fabricated of a good thermal conductor, such as a metal, for instance, copper or a metal alloy, such as a copper alloy. Heat transfer base 420 includes a heat transfer surface 421, sized and configured to couple to electronic component(s) 401 to be cooled. By way of example, heat transfer surface 421 can be a flat, lower surface of heat transfer base 420, which is appropriately sized to couple and substantially cover the electronic component(s) to be cooled. A plurality of thermally-conductive fins 423 extend, in one or more embodiments, from a surface 422 of heat transfer base 420 opposite to heat transfer surface 421. In the depicted embodiment, the plurality of thermally-conductive fins 423 are a plurality of thermally-conductive plate fins oriented substantially parallel, with channels defined between adjacent thermally-conductive plate fins. Note that the concepts disclosed herein can be used in association with other thermally-conductive fin configurations, as well.

In the embodiment depicted, joining material 435, such as a braze or solder material, is sized to overlie the footprint of the plurality of thermally-conductive fins 423, and is disposed between the fins and cover 440. Note that joining material 435 and/or joining material 435' (of FIGS. 4B-4D) refers to any material to facilitate joining, and/or a joint formed between, the plurality of thermally-conductive fins 423 and cover 440, such as during brazing, soldering, metal-metal diffusion bonding, resistance welding (RF), laser sealing and/or welding, etc. Note also that in one or more other embodiments, multiple smaller co-planar sheets of joining material 435 could be disposed between the fins and cover 440. During fabrication, a same or different joining material (e.g., braze material) can also be provided within a circumferential groove 425 formed in surface 422, sized and configured to receive an edge of cover 440 to facilitate hermetically sealing cover 440 to heat transfer base 420.

Figure 4B:
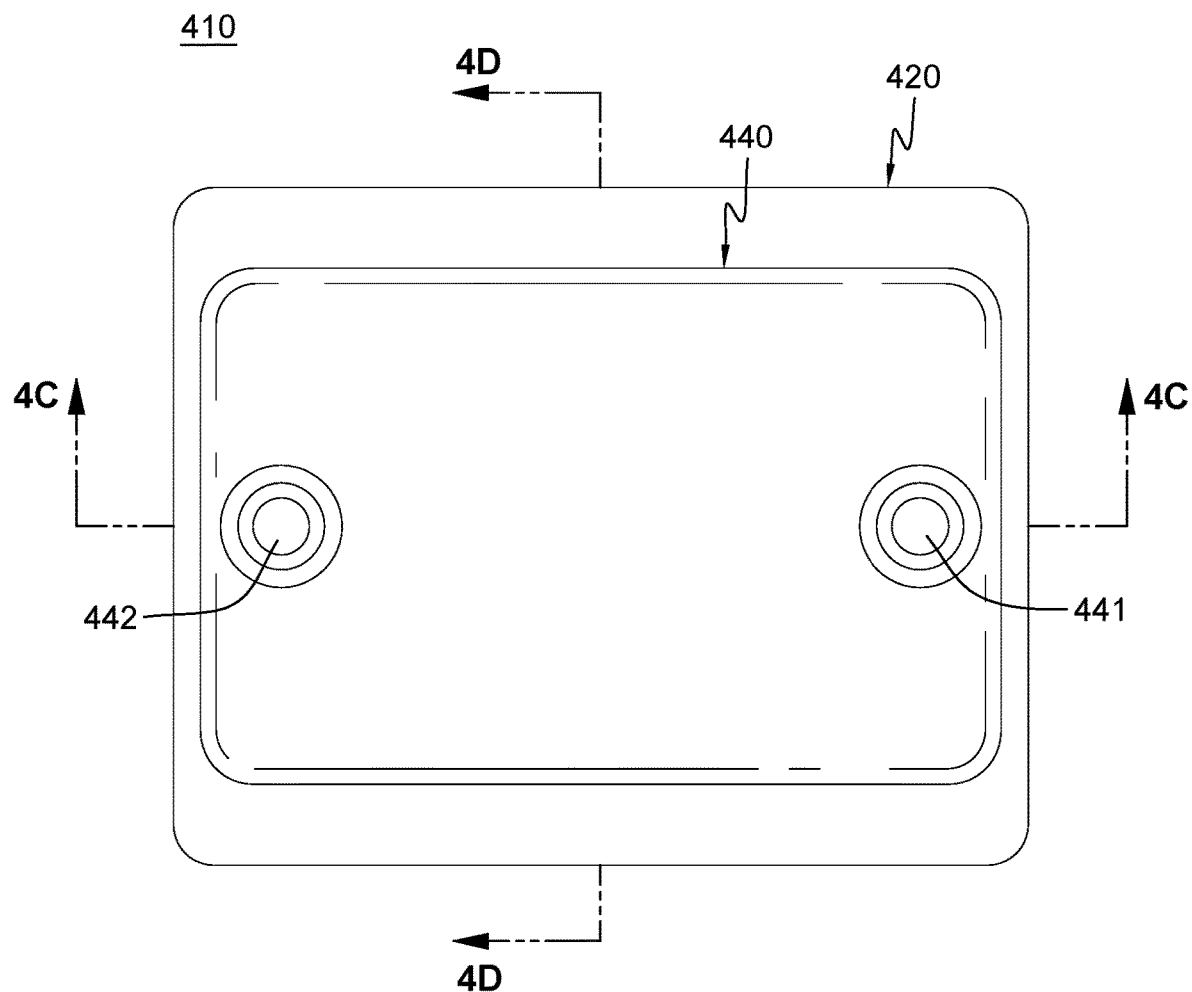
FIG. 4B is a plan view of the coolant-cooled heat sink of FIG. 4A.
Figure 4C:
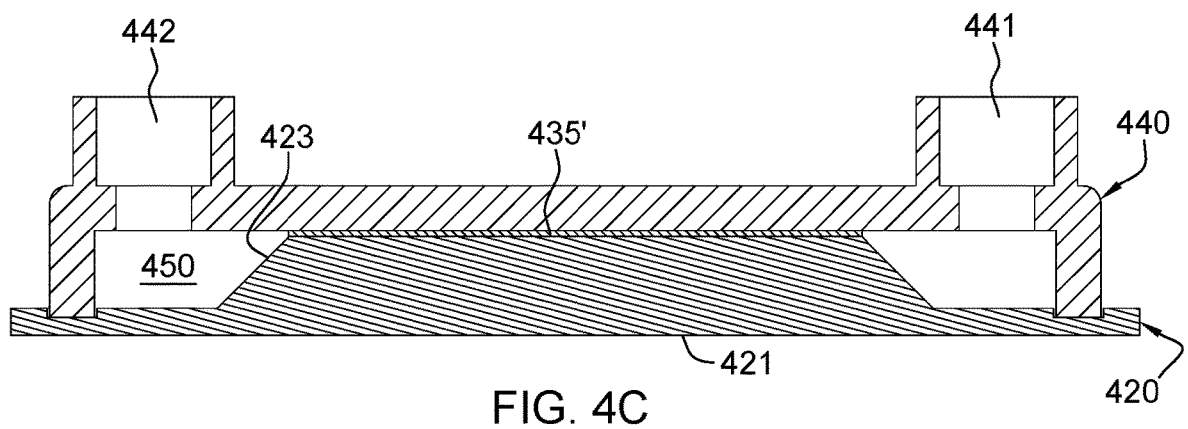
FIG. 4C is a cross-sectional elevational view of the coolant-cooled heat sink of FIG. 4B, taken along line 4C-4C thereof.
Figure 4D:
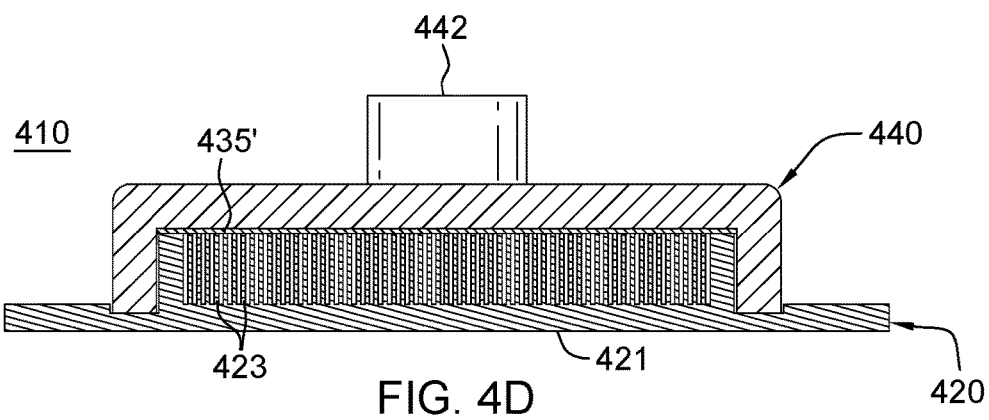
FIG. 4D is a cross-sectional elevational view of the coolant-cooled heat sink of FIG. 4B, taken along line 4D-4D thereof.

FIGS. 4B-4D depict coolant-cooled cold plate 410 after assembly and sealing of cover 440 to heat transfer base 420. Referring collectively to FIGS. 4B-4D, cover 440 and heat transfer base 420 are configured to define an internal coolant-carrying compartment 450 between the cover and base with sealing of the cover to the base using, for instance, a joining material, as described herein. In one or more embodiments, as part of the sealing process, the coolant-cooled heat sink assembly is heated in order to melt the joining material(s), including the joining material disposed between the plurality of thermally-conductive fins 423 and cover 440. By way of specific example, the joining material can be an industrial braze alloy, such as BCuP-5, and the sealing process can include placing the assembly with the braze material between the fins and cover 440 in a belt furnace, and raising the temperature of the assembly within the belt furnace from, for instance, starting room temperature to at or above the melting temperature of the braze alloy. For instance, BCuP-5 has a melting temperature of approximately 800° C., and so, the belt furnace can raise the temperature of the assembly to, for instance, 805° C. or 810° C. peak for a few seconds, after which the furnace is shut down and the assembly is allowed to cool. In one implementation, raising the temperature to 805°-810° C. might require 25-30 minutes, and cooling time may be, for instance, 45-60 minutes.

The sealing process results in the melted, and then cooled, joining material 435' joining the thermally-conductive fins 423 to cover 440 in order to, in part, provide a fluid-tight seal of thermally-conductive fins 423 to cover 440, thereby ensuring that coolant flowing through coolant-cooled heat sink 410 between a coolant inlet 441 and a coolant outlet 442 passes through the gaps between the thermally-conductive fins 423, and not over the fins. Once cooled, the resultant coolant-cooled structure of FIGS. 4C & 4D is obtained, with the melted and cooled joining material 435' forming a bond or joint between thermally-conductive fins 423 and cover 440.

As fin pitch continues to decrease to improve thermal performance, there is a possibility for bacteria to collect and grow (such as a biofilm) on one or more thermally-conductive fins of the coolant-cooled heat sink. One solution to preventing bacteria growth is to treat the coolant with a biocide. However, in a closed loop coolant implementation, such as a closed loop aqueous-based coolant implementation, it may not be possible to use a standard biocide treatment to control bacterial growth over the life of the coolant within the coolant-cooled heat sink, and in particular, on one or more thermally-conductive fins within the coolant-carrying compartment of the coolant-cooled heat sink. Without a biocide, there is a possibility for coolant channel fouling to occur over the operational lifetime of the coolant or coolant-cooled heat sink, particularly resulting in a performance degradation of the heat sink. Another possible solution is to provide long-term maintenance of the cooling system, such as by periodically replacing one or more components of the cooling system in order to maintain heat transfer capability of the cooling system, and in particular, the coolant-cooled heat sink(s). As a further option, an ultra-violet (UV) light source could be installed in the cooling system, separate from the coolant-cooled heat sink, in order to treat coolant within the coolant loop. This solution can be effective in mitigating bacteria, but could still allow biofilm accumulation within the coolant-cooled heat sink fin channels, potentially leading to an unacceptable degradation in heat transfer capability of the heat sink. Also, uncontrolled UV light application can lead to degradation of a corrosion inhibitor within the coolant loop, such as Benzotriazole (BTA), which is used in one embodiment of an aqueous-based coolant solution for a cooling system, such as disclosed herein.

Disclosed herein, in one or more embodiments, is an apparatus which includes an ultra-violet (UV) light assembly in association with, or integrated with, a coolant-cooled heat sink of a cooling system for directing UV light towards an interior surface of the coolant-cooled heat sink across which the coolant passes. The UV light (or rays or radiation) dosage is controlled to prevent or inhibit bacterial growth at the interior surface of the coolant-cooled heat sink while, in one or more embodiments, also balancing against degradation of anti-corrosion material in the coolant to maintain the anti-corrosion material active in the coolant above a set threshold for a specified operational life of the coolant or cooling system. In one embodiment, ultra-violet (UV) light dosage, including intensity and time-duration of UV light application, is controlled in order to mitigate or inhibit bacterial growth at one or more surfaces of the thermally-conductive fins, as well as preserving anti-corrosion material effectiveness within the coolant. In one or more embodiments, the ultra-violet (UV) light assembly control is programmed or configured to provide a desired UV light intensity and time-duration onto the interior surface of the coolant-cooled heat sink, taking into account any UV light absorption in the coolant, the desired light intensity and uniformity to be applied to the interior surface of the coolant-cooled heat sink, and the effective dosage and schedule desired. In one or more implementations, the control provides a periodic application of UV light onto the interior surface of the coolant-cooled heat sink in order to prevent or inhibit bacterial collection and growth, such as a biofilm growth, particularly on one or more fins of the plurality of thermally-conductive fins of the coolant-cooled heat sink, while maintaining the anti-corrosion material within the coolant active for a specified lifetime of the coolant.

Advantageously, the apparatuses disclosed herein include one or more coolant-cooled heat sinks with an ultra-violet (UV) light assembly associated or integrated therewith to provide a desired UV light dosage onto an interior surface of the coolant-cooled heat sink to inhibit bacterial growth at the interior surface of the coolant-cooled heat sink. In one embodiment, UV light uniformity and dosage are facilitated using one or more lenses and light sources associated or integrated with the coolant-cooled heat sink. The apparatuses disclosed ensure uniform UV dosing on a specific surface or area of an interior surface to prevent or inhibit biofilm buildup in one or more selected areas within the coolant-cooled heat sink. Further, a dosing schedule is predetermined to ensure that the UV light application is compatible with any anti-corrosion material within the coolant, for long-term coolant reliability. In addition, the apparatuses disclosed herein eliminate environmental and regulatory concerns with using a biocidal agent in the field for the cooling system applications described. In one or more implementations, the UV light assembly includes a control, which is programmed or configured with ON/OFF intervals as required to vary UV light dosage as desired. The apparatuses disclosed advantageously inhibit, or even eliminate, any possible long-term clogging of channels between thermally-conductive fins within the coolant-cooled heat sink, thereby improving system reliability by reducing, or eliminating, any associated thermal degradation resulting from clogging. Further, in one or more implementations, the UV light source can be coupled to the coolant-cooled heat sink outside the coolant-carrying compartment, and thus be replaceable, if desired.

Figure 5A:
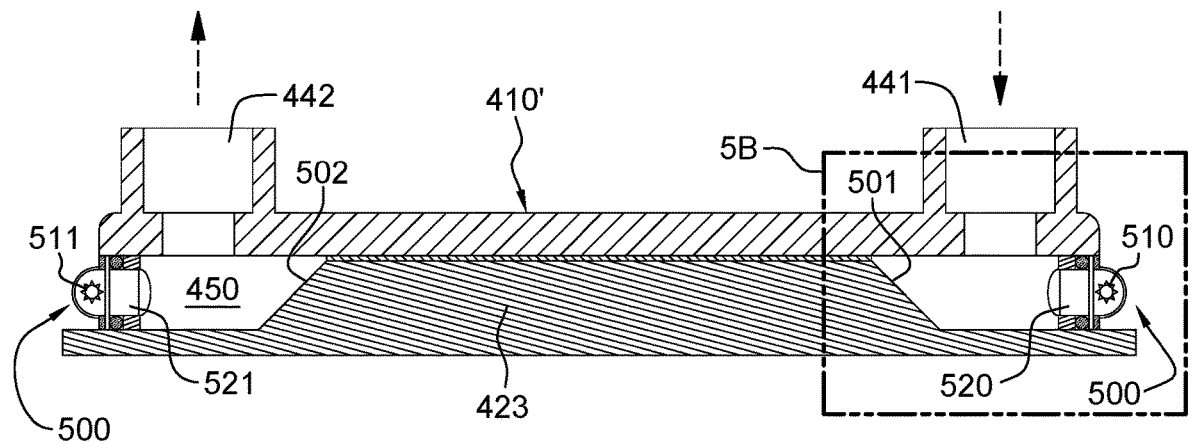
FIG. 5A depicts a cross-sectional elevational view of one embodiment of an apparatus including a coolant-cooled heat sink such as depicted in FIGS. 4A-4D, and an associated ultra-violet (UV) light assembly, in accordance with one or more aspects of the present invention.
Figure 5B:
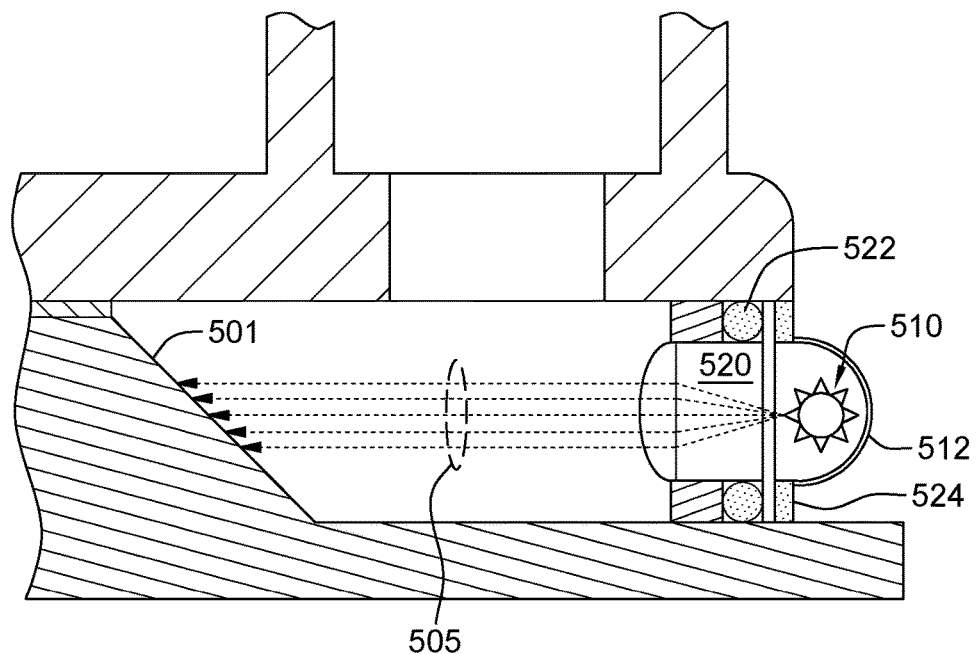
FIG. 5B is an enlarged view of the apparatus of FIG. 5A, taken along line 5B thereof, in accordance with one or more aspects of the present invention.

FIGS. 5A-5B depict one embodiment of an apparatus which includes a coolant-cooled heat sink 410', such as coolant-cooled heat sink 410 described above in connection with FIGS. 4A-4D, and an ultra-violet (UV) light assembly 500 associated (or integrated) therewith for directing UV light towards an interior surface of coolant-cooled heat sink 410' across which coolant passes. In the embodiment illustrated, the ultra-violet (UV) light assembly is configured and positioned to direct UV light towards the plurality of thermally-conductive fins 423 disposed within coolant-carrying compartment 450 of coolant-cooled heat sink 410'. As illustrated, a UV light source 510 is positioned (or optically coupled) to provide UV light through a lens 520, such as a UV lens (e.g., quartz lens) into the interior coolant-carrying compartment 450 of coolant-cooled heat sink 410' at (for instance) a coolant inlet side 501 of the plurality of thermally-conductive fins 423, with the coolant inlet side 501 receiving coolant via coolant inlet 441. Similarly, another UV light source 511 of UV light assembly 500, and an associated lens 521, are positioned (or optically coupled) at the coolant outlet side 502 of thermally-conductive fins 423 adjacent to coolant outlet 442, of coolant-cooled heat sink 410' for directing (in one embodiment) UV light onto the plurality of thermally-conductive fins 423 at the coolant outlet side 502 of the thermally-conductive fins.

In one or more embodiments, the ultra-violet (UV) light can be ultra-violet C light, rays, radiation, with a wavelength in the range of 100-280 nm. The UV light selected, as well as dosage (intensity and duration) can be set for a particular application in order to facilitate inhibiting or preventing bacterial growth at the selected interior surface of the coolant-cooled heat sink, such as described herein. In one or more embodiments, the interior surface includes one or more surfaces of the thermally-conductive fins within the coolant-cooled heat sink at the coolant inlet side and/or coolant outlet side of the thermally-conductive fins. In this manner, fin clogging due to bacterial growth is prevented, thereby improving reliability of the coolant-cooled heat sink over the operational lifetime of the heat sink.

In one or more embodiments, UV light is selectively (e.g., periodically) introduced through the respective lens 520, 521, into the interior compartment of coolant-cooled heat sink 410', onto the respective interior surfaces of the coolant-cooled heat sink, which as noted, in one embodiment are respective surfaces of the plurality of thermally-conductive fins within the coolant-carrying compartment. As illustrated, in one embodiment, each lens 520, 521 is a collimating lens configured to create a substantially uniform UV light 505 for impingement on the respective interior surface(s), such as on the edge surfaces of the plurality of thermally-conductive fins 423 at the coolant inlet and outlet sides 501, 502 of coolant-cooled heat sink 410'. In one or more implementations, the lens 520, 521 are sized and configured to project a set or desired pattern of UV light onto the respective interior surface of the coolant-cooled heat sink in order to, for instance, prevent, or inhibit, bacterial growth on the interior surface of the coolant-cooled heat sink. As illustrated, in one embodiment each lens 520, 521 is sealed to the heat sink via a respective O-ring seal 522, which provides a fluid-tight seal of the lens to the coolant-carrying heat sink 410'. A respective retaining ring 524, such as a threaded retaining ring, or other type of locking retaining ring, can be employed to retain lenses 520, 521 in position within the coolant-cooled heat sink 410'. In addition to directing (in one embodiment) a uniform intensity UV light onto the desired interior surface(s) of the thermally-conductive fins, such as at the coolant inlet side and/or coolant outlet side, lenses 520, 521 are positioned to reside a desired fixed distance from the interior surface at issue. For instance, each lens can be 5 cm or less (e.g., approximately 1 cm) from the respective fins, in order to minimize light absorption or loss in the coolant flowing through the coolant-carrying compartment, and thereby facilitate application of the desired UV light dosage.

In one embodiment, UV light source 510 can be, or include, ultra-violet light-emitting diodes (LEDs), or other type of UV light source, such as a gas-discharge lamp, an arc lamp or tube, etc. As illustrated in FIG. 5B, a UV lamp enclosure, including a reflector 512, can be provided to facilitate coupling the UV light source to the heat sink and facilitate directing UV light into lens 520, and hence onto the desired interior surface(s) of the coolant-cooled heat sink 410'. In one embodiment, the enclosure can be mechanically attached or coupled to the heat sink. In one implementation, a lower-power UV light source 510, 511 is used to generate the desired UV light, such as a 40 mW/cm² UV light dosage, with the light dosage being periodically applied as desired to inhibit bacterial growth at the interior surface of the coolant-cooled heat sink, while maintaining anti-corrosion material within the coolant active for the specific lifetime of the coolant.

Figure 6A:
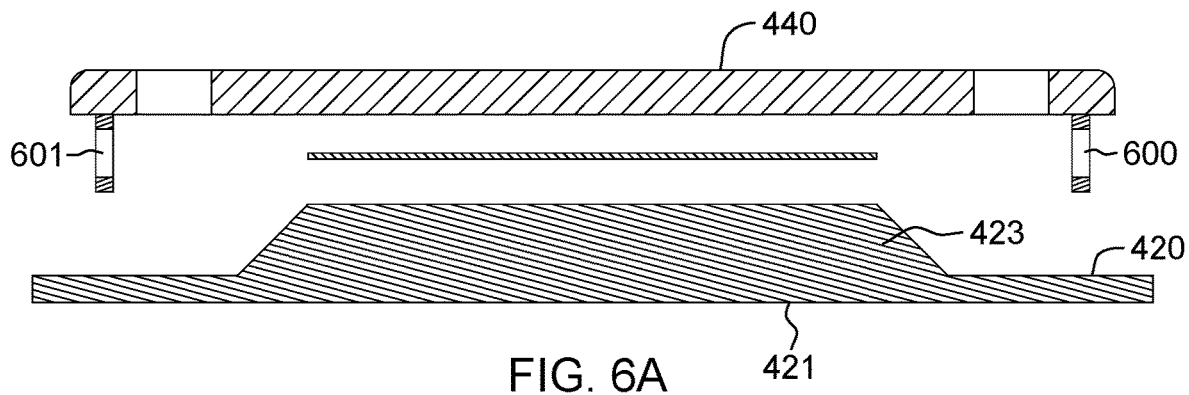
FIGS. 6A-6C illustrate one embodiment of fabricating the apparatus of FIGS. 5A & 5B, in accordance with one or more aspects of the present invention.
Figure 6B:
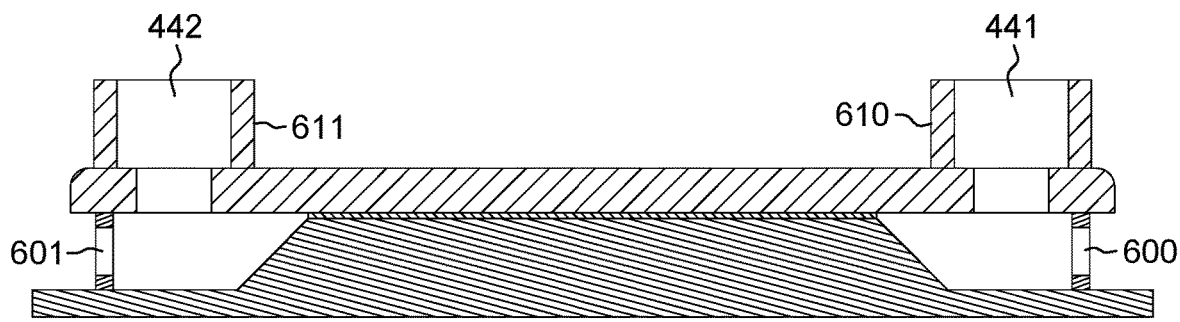
Figure 6C:
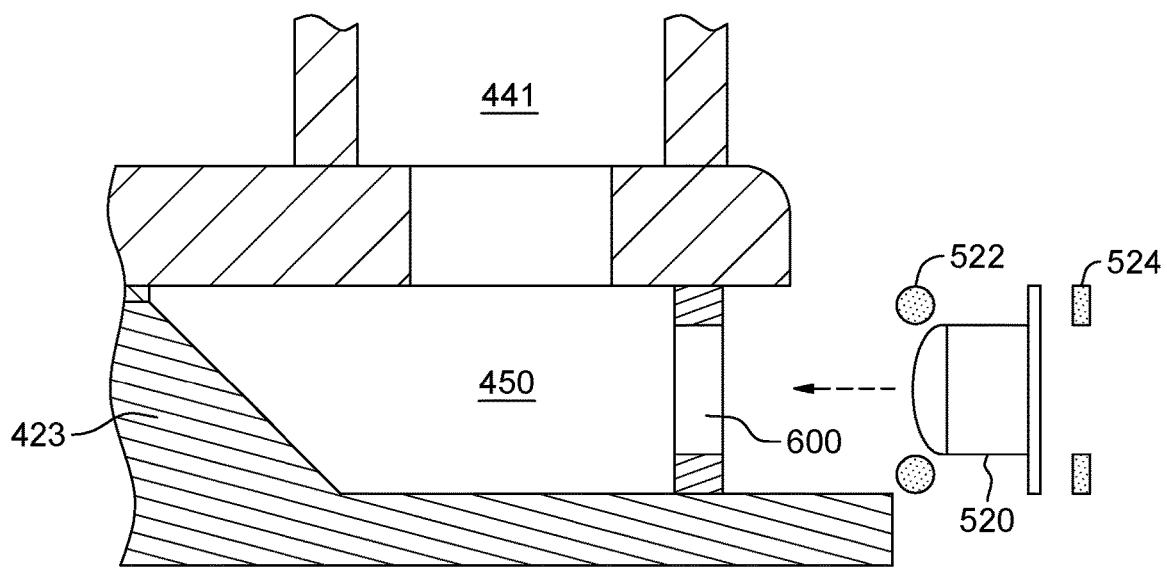

FIGS. 6A-6C depict one embodiment of fabricating an apparatus such as depicted in FIGS. 5A-5B. As illustrated in FIG. 6A, heat transfer base 420 is provided (in one embodiment) with a plurality of thermally-conductive fins 423, as well as a cover 440, which includes openings for the coolant inlet and coolant outlet hose barb connections, as well as openings 600, 601, each to receive a respective lens of the UV light assembly. Standard manufacturing techniques can be used to provide the heat transfer base 420 and cover 440 in the desired configuration. As illustrated in FIG. 6B, cover 440 is secured to heat transfer base 420 using, for instance, brazing and heating, as described above. Additionally, in one or more implementations, hose barb fittings 610, 611 are secured (e.g., by brazing and heating) to the respective openings in cover 440 to facilitate defining coolant inlet 441 and coolant outlet 442.

FIG. 6C illustrates O-ring 522 and lens 520 being inserted into opening 600 and secured to coolant-cooled heat sink 410' using a retaining ring 524, such as a threaded retaining ring. As illustrated in FIGS. 5A & 5B, lens 520 is configured to extend into, and in one embodiment, partially through opening 600 in cover 440 to facilitate directing UV light onto the respective interior surface(s) the coolant-cooled heat sink, such as onto one or more surfaces of the plurality of thermally-conductive fins 423 within coolant-carrying compartment 450 in this example. The O-ring 522, lens 520 and retaining ring 524 are respectively sized and configured to form a fluid-tight seal with, for instance, the sidewall of the resultant coolant-cooled heat sink.

FIG. 7A depicts a further embodiment of a cooled electronic system 700, similar in one or more embodiments to cooled electronic system 200 described above in connection with FIGS. 2A-3. By way of example, cooled electronic system 700 includes memory cards 701, and power supply and input/output circuitry 702, as well as multiple coolant-cooled heat sinks (or cold plates) 710 (CP1-CP4), coupled to respective heat-generating electronic components to be cooled (not shown). In one implementation, coolant-cooled heat sinks 710 are substantially identical, or similar to, coolant-cooled heat sink 410' described above in connection with FIGS. 5A-6C. In the implementation of FIG. 7A, the UV light assembly 500' further includes an ultra-violet (UV) power supply 720, with a control 722 for controlling application of UV light to the respective coolant-cooled heat sinks 710. In one or more embodiments, UV light application is controlled by control 722 using (or based on) UV light intensity sensing and feedback provided by one or more UV light sensors 721 associated with one or more of the ultra-violet (UV) light sources 510. In one embodiment, control 722 controls the application of power, via power lines 724, to UV light sources 510. In one or more implementations, control 722 can be a microcontroller-implemented control facility and/or other control system-implemented facility disposed within the UV power supply 720 or remote from the UV power supply, but in operative communication therewith. By providing UV light intensity feedback to control 722, the UV light assembly 500' is able to ensure that the desired UV light intensity continues to be supplied to the respective interior surface of the coolant-cooled heat sinks over the lifetime of the system. In one implementation, the UV light sensor 721 can be, or include, a photodiode UV sensor unit, such as an InGaAs photodiode array.

Figure 7B:
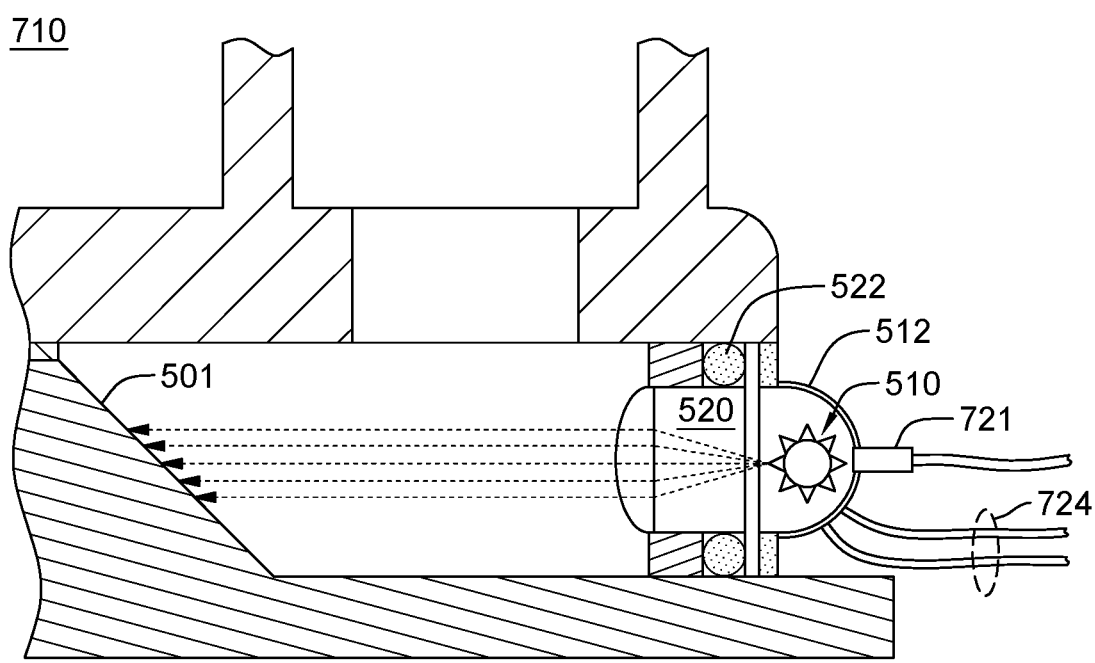
FIG. 7B is a partial depiction of one coolant-cooled heat sink and associated components of one embodiment of an ultra-violet light assembly, in accordance with one or more aspects of the present invention.

FIG. 7B depicts one embodiment of coolant-cooled heat sink 710, where coolant-cooled heat sink 710 is substantially identical to coolant-cooled heat sink 410' described above in connection with FIGS. 5A-6C, with the exception of UV light sensor 721 coupled to provide UV light intensity feedback data to the UV light assembly control 722, such as depicted in FIG. 7A.

In the implementation of FIGS. 7A & 7B, UV light intensity sensor 721 and control 722 provide intensity monitoring and dosage control for ensuring application of the desired UV light intensity (and duration) to one or more interior surfaces of the coolant-cooled heat sink. In one embodiment, UV light intensity loss from coolant absorption (e.g., water absorption) is predetermined and taken into account in determining the desired UV light dosage to be applied. For instance, at a water depth of approximately 1 cm, approximately 95% of the UV light intensity will reach the interior surface of interest. At a 2 cm distance, the light intensity at the interior surface will be approximately 90% of the UV light intensity passing through the lens.

Dosage or intensity monitoring can include use of, for instance, an optical fiber positioned adjacent to the UV source, with collected UV light being transmitted to a photodiode to generate a UV light intensity feedback signal to the UV light assembly control. Note that the measured UV signal output can be a portion of the total UV light output from the UV light source. In one implementation, relative change in intensity of the signal is tracked from installation to a current time, for instance, for monitoring for an early sign of UV light source or lamp intensity degradation. Where there is a UV light intensity change, power to the UV light source can be adjusted (e.g., increased) to account for the light source degradation. The UV light source can be calibrated for power output prior to (or at) install, and then a portion of the UV light output can be measured to determine the optimal (i.e., original) light source intensity, which is then used as the working point of reference for any potential degradation of the light source over the lifetime of the cooling system.

Figure 7C:
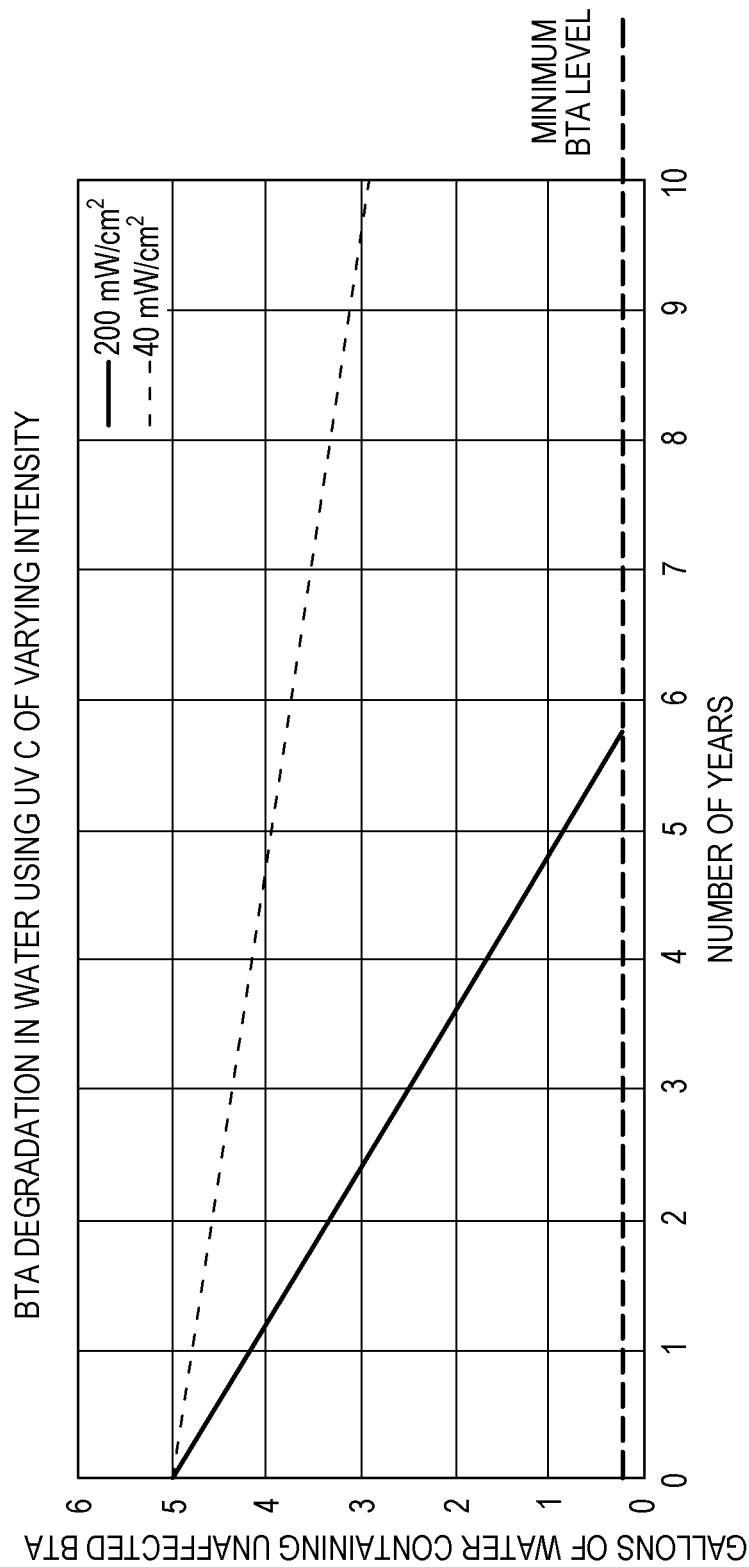
FIG. 7C is a graph illustrating effect of UV light intensity on anti-corrosion material over a coolant lifetime, in accordance with one or more aspects of the present invention.

FIG. 7C graphically illustrates effect of UV light intensity on an aqueous coolant which includes Benzotriazole (BTA), which is one embodiment of an ani-corrosion material that can be used within the coolant circulating through the heat sink. As illustrated in FIG. 7C, application of a 200 mW/cm$^2$ light intensity periodically to coolant with BTA can cause degradation of the BTA too quickly for a specified operational lifetime of the closed loop cooling system, such as a 10 year or more lifetime. Thus, maintaining the UV light intensity and uniformity at a desired lower level is advantageous to being able to both disinfect or inhibit bacterial growth within the coolant-cooled heat sink, as well as maintain the desired anti-corrosion material levels (i.e., BTA levels) within the coolant passing through the coolant-cooled heat sink. In the example graph of FIG. 7C, a dosing schedule of a few times per week for a set number of minutes each time is assumed. As illustrated, the minimum acceptable BTA level is reached between years 5 and 6, with light intensity of 200 mW/cm$^2$, whereas by applying a lower UV light intensity of (for instance) 40 mW/cm$^2$, the minimum BTA level is not be reached until well after the specified lifetime of the cooling system, such as well after 10 years, in one example.

As noted, in one or more embodiments, ultra-violet (UV) C light is used to periodically treat one or more interior surfaces of the coolant-cooled heat sink in order to maintain the interior surface, such as the thermally-conductive fins, free of bacteria, thereby allowing coolant to readily flow through or across the fins. The ultra-violet (UV) dose (mJ/cm$^2$) can be determined as the product of light intensity (Watt/cm2)×residence time. A reasonable UV dose for prevention of bacteria accumulation on a surface is approximately 40 mJ/cm$^2$. Therefore, using a UV C light source capable of producing 20 mW/cm$^2$, the source might be operated for a period of two seconds in order to achieve a dose of 40 mJ/cm$^2$. For instance, pursuant to the International Ultra-Violet Association, it is accepted that a dose of 40 mJ/cm$^2$ of 254 nm light will remove 99.99% of any pathogenic microorganism.

FIG. 8 depicts a further embodiment of a cooled electronic system 700' similar (in part) to cooled electronic system 700 of FIG. 7A. By way of example, cooled electronic system 700' includes memory cards 701, and power supply and input/output circuitry 702, as well as coolant-cooled heat sinks 710 (CP1-CP4), which are coupled to respective heat-generating electronic components to be cooled (not shown).

In the implementation of FIG. 8, ultra-violet (UV) light assembly 500" includes, by way of further example only, a single ultra-violet light source 800 and light guides 810 to distribute UV light from UV light source 800 to the individual coolant-cooled heat sinks 710. In one implementation, the UV light guides 810 include multiple individual, heat-sink-level light guides 811, that are described further below with reference to FIGS. 9A-10F. The light guides facilitate distributing UV light from UV light source 800 to the respective interior surfaces of the coolant-cooled heat sinks to be dosed with UV light. In one or more embodiments, the UV light guides 810, 811 are made of a transparent material, such as glass or plastic, and can be, in one implementation, thin filaments capable of transmitting light through internal reflection.

As with the light assembly embodiment of FIG. 7A, UV light assembly 500" of cooled electronic system 700' of FIG. 8 further includes an ultra-violet (UV) power supply 720, with a control 722 for controlling application of UV light to the respective coolant-cooled heat sinks 710. In one or more embodiments, UV light dosage is controlled by control 722 based on UV light intensity sensing via one or more UV light sensors 721 associated with UV light source 800. Control 722 controls power (via power supply lines 724) to UV light source 800, and thus, intensity of the provided UV light. With the UV light intensity feedback to control 722, the control ensures supply of the desired UV light intensity to the respective interior surfaces of the coolant-cooled heat sinks. As noted above, the UV light source and the UV light sensors can be any of a variety of available ultra-violet (UV) light sources and UV light sensors, depending on the particular application.

FIGS. 9A-9D depict another embodiment of coolant-cooled heat sink 710, where the coolant-cooled heat sink is similar, or substantially identical, to coolant-cooled heat sink 410' described above in connection with FIGS. 5A-6C. A difference is in the provision of heat-sink-level UV light guides 811 (and micro-lenses 900 at the ends of the light guides (see FIG. 9B)) for distributing the UV light from UV light source 800 onto the respective interior surfaces of the coolant-cooled heat sinks. In this embodiment, a single UV light source 800 is shared by multiple coolant-cooled cold plates 710. Further, the number and placement of UV light guides 811, relative to the interior surface to be protected, can vary as needed. In the exemplary embodiment of FIGS. 9A-9D, ten individual heat-sink-level light guides 811 are illustrated for directing UV light from UV light source 800 into the coolant-carrying compartment and onto one or more selected surfaces of the plurality of thermally-conductive fins. Note that the size of the individual UV light guides 811, as well as the number of UV light guides integrated with a particular coolant-cooled heat sink 710 can vary, depending on the application. As noted, at the end of each UV light guide 811, disposed at the coolant-carrying compartment, a micro-lens 900 can be provided to, for instance, facilitate collimating light emitting from the respective UV light guide 811. In this manner, a desired uniform distribution of UV light can be provided onto the respective interior surface (or surfaces), spaced from the ends of the UV light guides within the coolant-cooled heat sink.

Figure 9A:
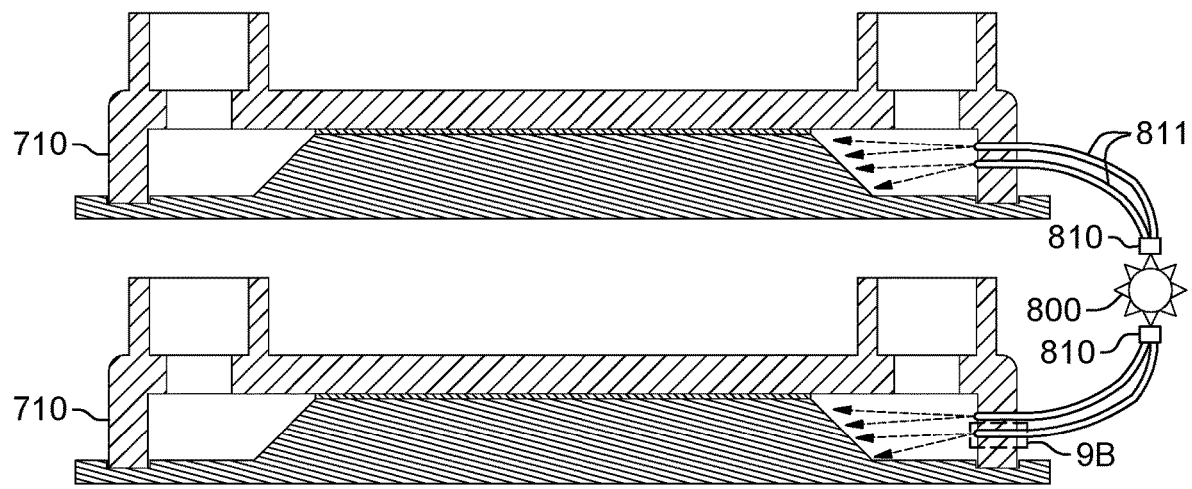
FIGS. 9A-9D illustrate another embodiment of an apparatus including a coolant-cooled heat sink and an associated ultra-violet (UV) light assembly, in accordance with one or more aspects of the present invention.
Figure 9B:
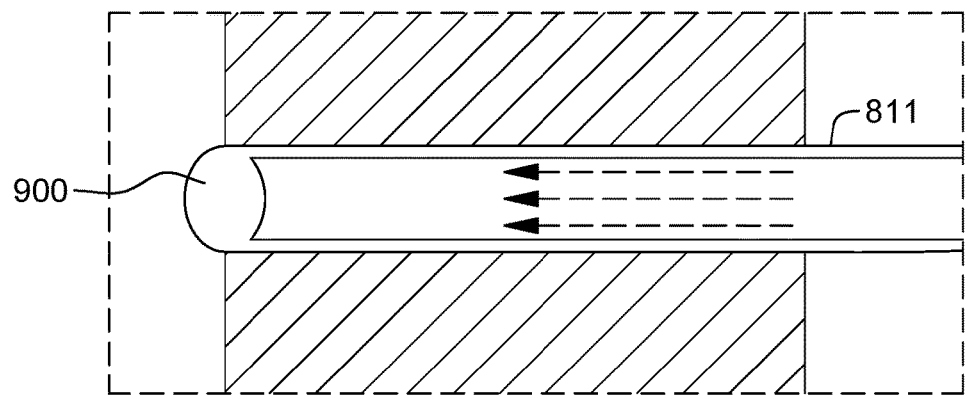
Figure 9C:
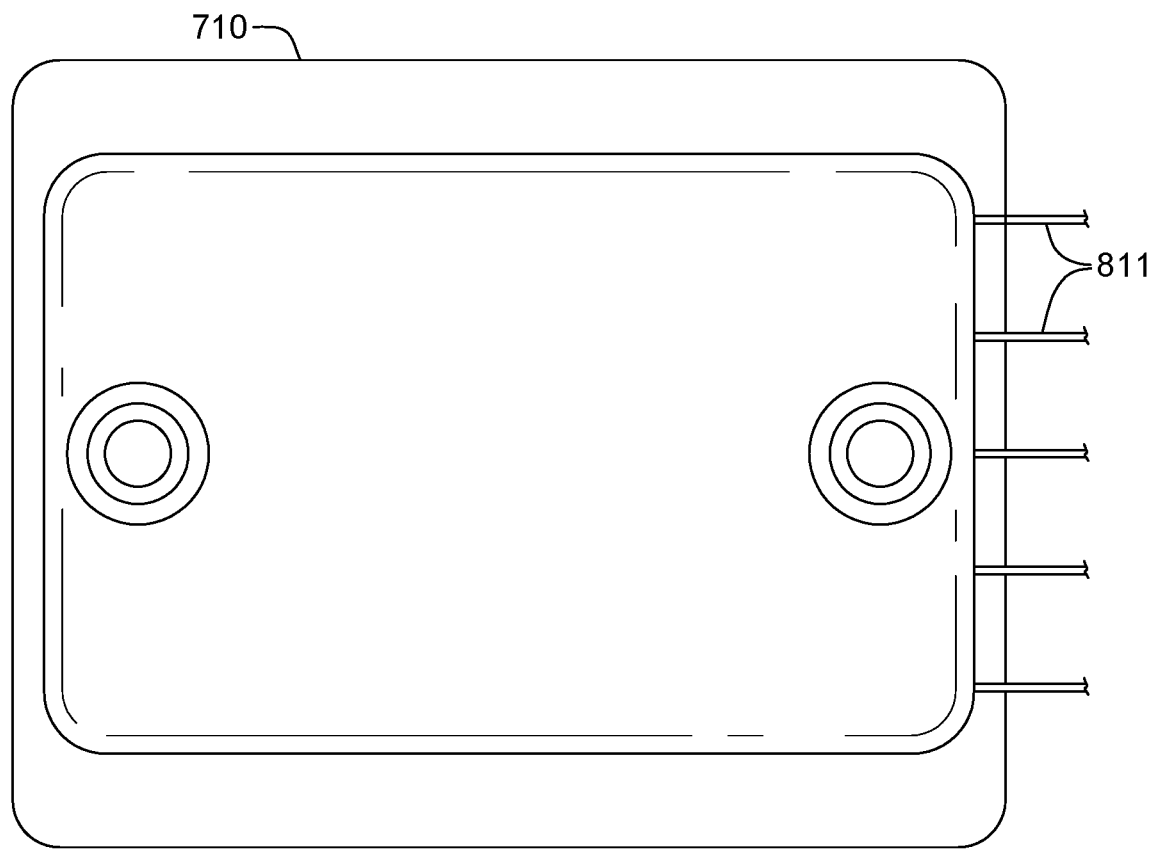
Figure 9D:
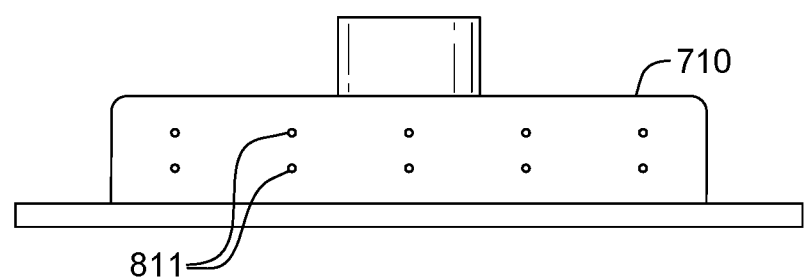
Figure 10A:
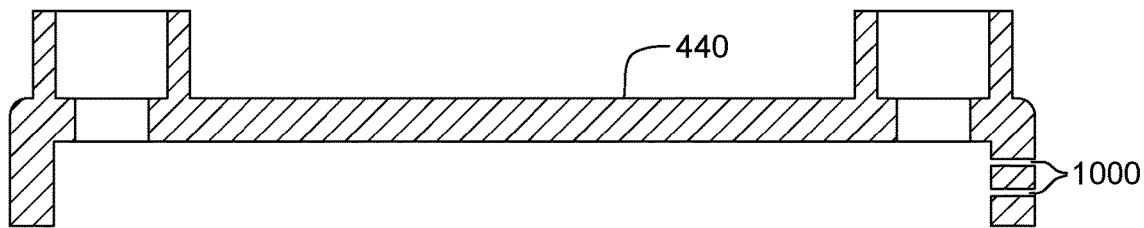
FIGS. 10A-10F depict one embodiment of fabricating the apparatus of FIGS. 9A-9D; in accordance with one or more aspects of the present invention.
Figure 10B:
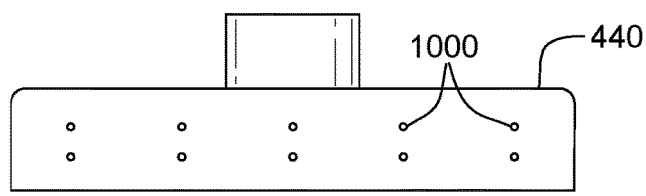
Figure 10C:
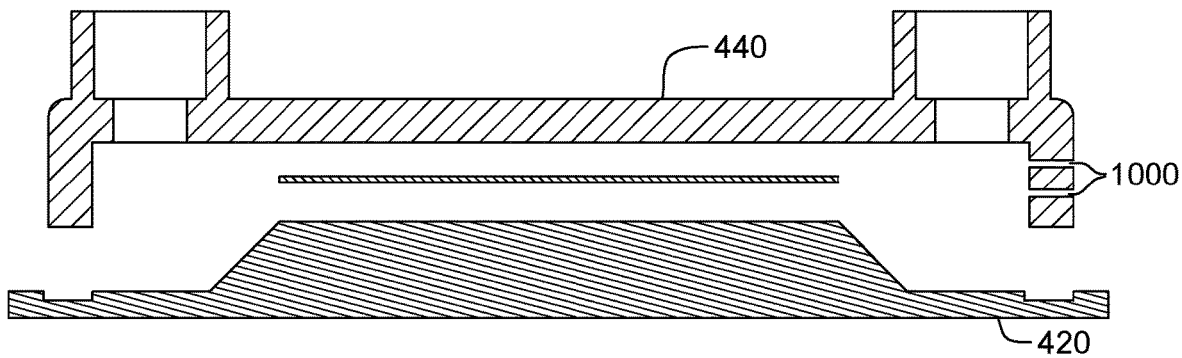
Figure 10D:
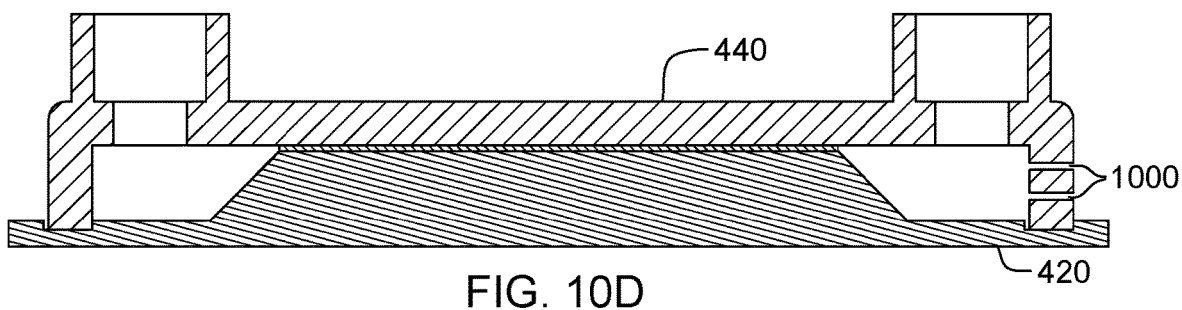
Figure 10E:
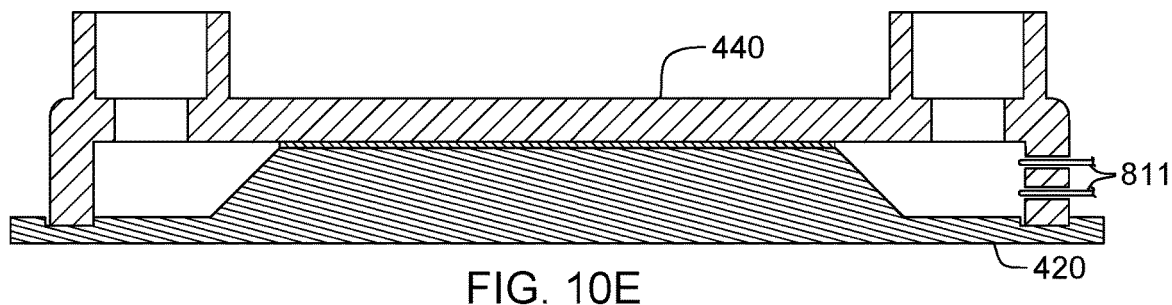
Figure 10F:
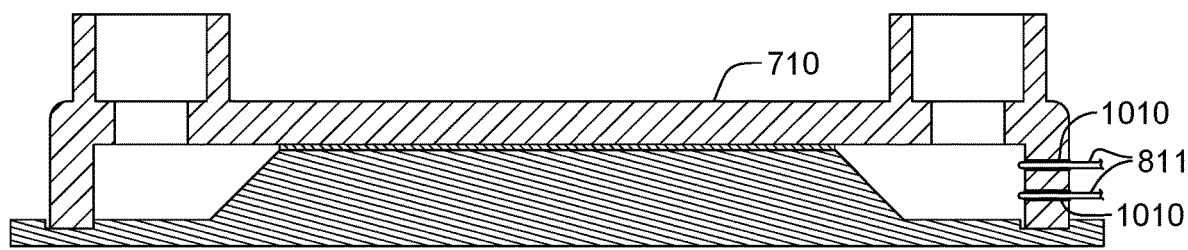

FIGS. 10A-10F depict one embodiment of fabricating an apparatus including multiple coolant-cooled heat sinks and an ultra-violet (UV) light assembly, such as depicted in FIGS. 8-9D. As illustrated in FIGS. 10A-10F, a cover 440, and a heat transfer base 420 with a plurality of thermally-conductive fins are provided in the desired configuration using, in one embodiment, standard manufacturing techniques, such as noted above. In one or more embodiments, the cover and heat transfer base are fabricated of a metal material, and the fabrication approach includes providing a plurality of holes 1000 in cover 440 sized and positioned to receive respective UV light guides. In the fabrication approach presented, the plurality of holes 1000 can be provided by, for instance, drilling cover 440. Note that holes 1000 are in addition to the openings (not shown) for the coolant inlet and coolant outlet, such as described above. As illustrated in FIGS. 10C & 10D, cover 440 is secured to heat transfer base 420 using, for instance, braising and heating, as described above. As shown in FIG. 10E, the UV light guides 811 are inserted into the respective openings 1000 in cover 440, and sealed using a sealing material 1010 or plug, such as an epoxy, in order to provide fluid-tight seals around the heat-sink-level UV light guides 811.

Figure 11:
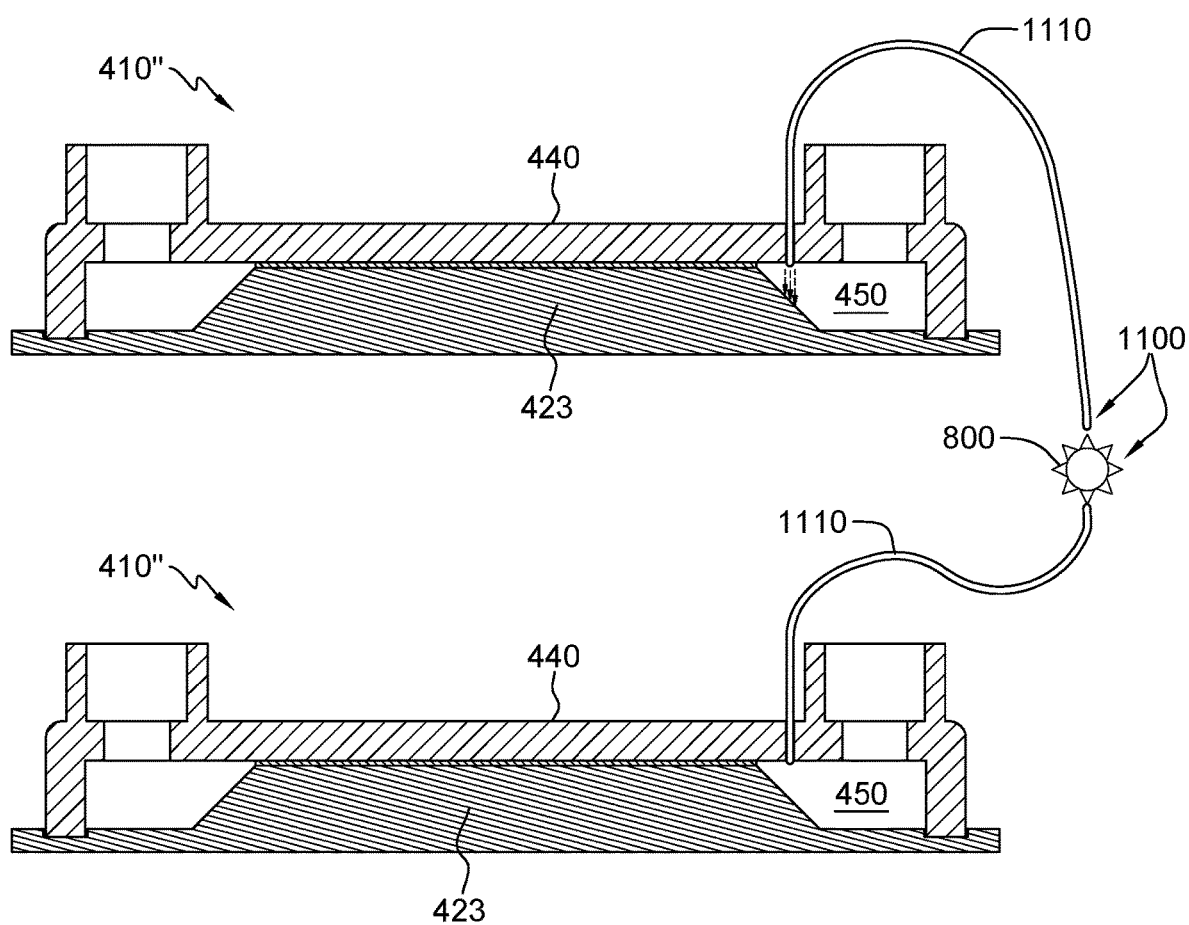
FIG. 11 depicts another embodiment of an apparatus including multiple coolant-cooled heat sinks and an associated ultra-violet (UV) light assembly, in accordance with one or more aspects of the present invention.

FIG. 11 depicts another embodiment of an apparatus including multiple coolant-cooled heat sinks 410", such as coolant-cooled heat sink 410 described above in connection with FIGS. 4A-4D, and an ultraviolet (UV) light assembly 1100 associated or integrated therewith for directing UV light towards selected interior surfaces of the coolant-cooled heat sinks 410" across which coolant passes. In the embodiment illustrated, the ultra-violet (UV) light assembly 1100 includes UV light source 800 configured to generate UV light for multiple coolant-cooled heat sinks 410". As illustrated, one or more heat-sink-level UV light guides 1110 (similar to heat-sink-level UV light guides 811 discussed above) are configured and positioned to direct UV light from UV light source 800 into the coolant-carrying compartment 450 of the respective coolant-cooled heat sink 410" and onto the desired interior surface, such as onto one or more surfaces of the plurality of thermally-conductive fins 423 within the coolant-carrying compartment. In this implementation, UV light guides 1110 extend into the respective coolant-cooled heat sink via respective openings in an upper surface of cover 440, such that UV light is directed downwards onto the angled edge surfaces of the plurality of thermally-conductive fins at, for instance, the coolant inlet side and/or the coolant outlet side of the thermally-conductive fins. A water-tight seal or plug (not shown) is provided around each UV light guide 1110 in order to provide fluid-tight sealing of the light guides to the coolant-cooled heat sink. In one embodiment, one or more of the UV light guides, for instance, each light guide, has a micro-lens at the end of the guide or fiber to facilitate projecting a desired uniform UV light onto the interior surface at issue. For instance, in one or more embodiments, each UV light guide is provided with a collimating lens at the end of the UV light guide within the coolant-cooled heat sink. Although not shown, the UV light assembly 1100 of FIG. 11 can further include, in one or more embodiments, a UV power supply and a control, along with one or more UV light sensors (if desired), such as described above. For instance, the UV power supply and control, as well as the UV light sensors, can be similar to the UV power supply, control and sensors described above in connection with the embodiments of FIGS. 7A & 8.

As disclosed, apparatuses and methods of fabrication are provided herein which include a coolant-cooled heat sink through which coolant passes to facilitate cooling the coolant-cooled heat sink, and an ultra-violet (UV) light assembly associated with the coolant-cooled heat sink for directing UV light towards an interior surface of the coolant-cooled heat sink across which the coolant passes. The UV light inhibits bacterial growth at the interior surface of the coolant-cooled heat sink. In one embodiment, the UV light uniformity and dosage are facilitated using one or more lenses and light sources associated or integrated with the coolant-cooled heat sink. The UV light (or rays or radiation) dosage is controlled to prevent or inhibit bacterial growth at the interior surface of the coolant-cooled heat sink while, in one or more embodiments, also balancing against degradation of anti-corrosion material, such as Benzotriazole (BTA), in the coolant to maintain the anti-corrosion material active in the coolant above a set threshold for a specified operational life of the coolant or cooling system.

As noted, in one or more implementations, a control is provided for controlling UV light application to the selected interior surface(s) of the individual heat sinks. The control can be implemented as one or more microcontrollers associated with, or provided as part of, the UV power supply, or operatively coupled thereto. In one or more other implementations, any conventional computing environment can be used to implement UV light control processing (e.g., dosing), such as described herein.

Figure 12:
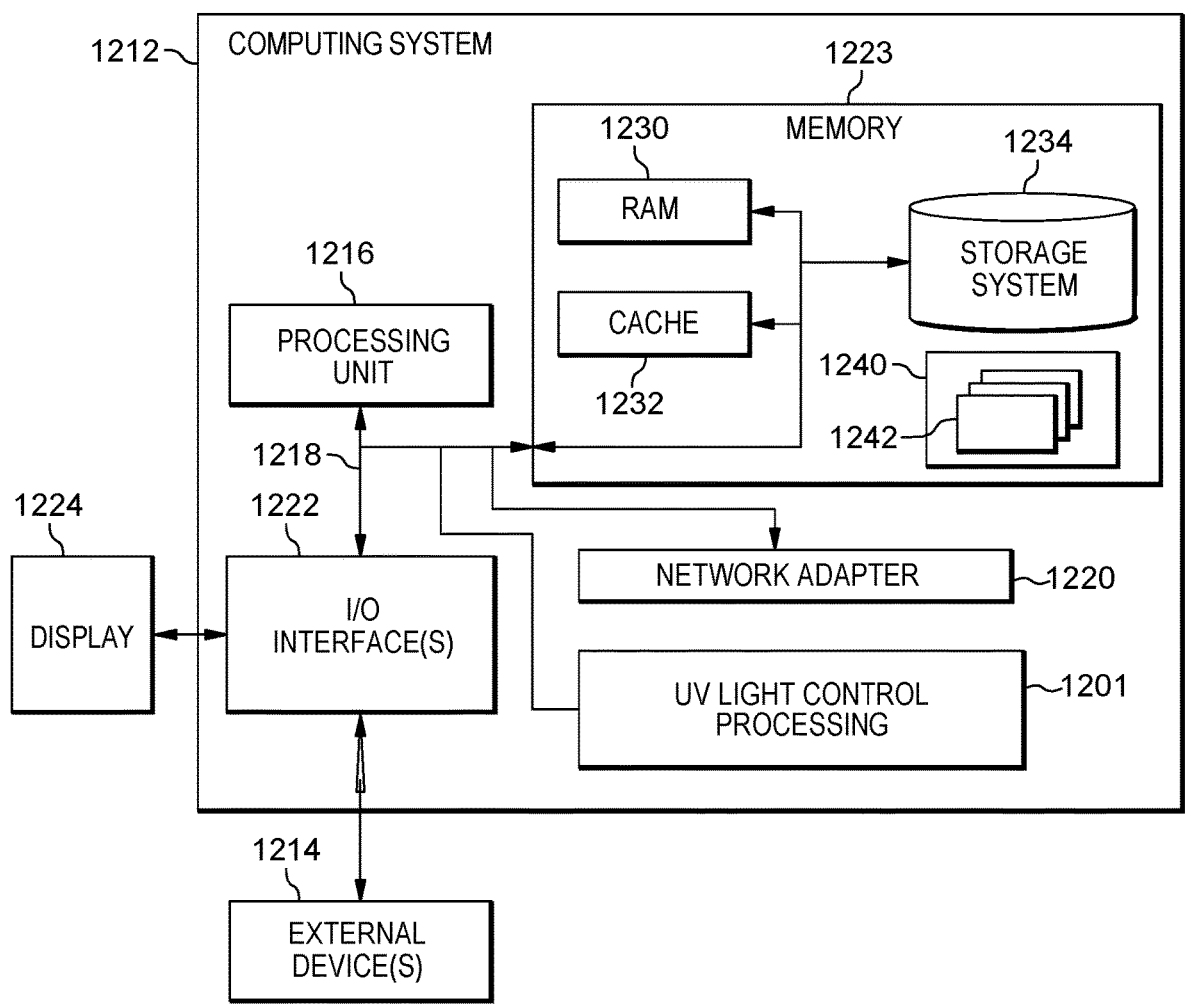
FIG. 12 depicts one embodiment of a computing system to implement, or facilitate implementing, ultra-violet (UV) light control, in accordance with one or more aspects of the present invention.

By way of further example, FIG. 12 depicts one embodiment of a computing environment 1200, which includes a computing system 1212. Examples of well-known computing systems, environments, and/or configurations that may be suitable for use with computer system 1212 include, but are not limited to, a server, a desktop computer, a work station, a wireless computer, a handheld or laptop computer or device, a mobile phone, a programmable consumer electronic device, a tablet, a personal digital assistant (PDA), and the like.

Computing system 1212 can be described in the general context of computer system-executable instructions, such as program modules, being executed by a computer system. Generally, program modules include routines, programs, objects, components, logic, data structures, and so on that perform particular tasks or implement particular abstract data types.

As depicted in FIG. 12, computing system 1212, is shown in the form of a general-purpose computing device. The components of computing system 1212 can include, but are not limited to, one or more processors or processing units 1216, a system memory 1223, and a bus 1218 that couples various system components including system memory 1223 to processor 1216.

In one embodiment, processor 1216 may be based on the z/Architecture® offered by International Business Machines Corporation, or other architectures offered by International Business Machines Corporation or other companies.

Bus 1218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computing system 1212 can include a variety of computer system readable media. Such media may be any available media that is accessible by computing system 1212, and it includes both volatile and non-volatile media, removable and non-removable media.

System memory 1223 can include computer system readable media in the form of volatile memory, such as random access memory (RAM) 1230 and/or cache memory 1232. Computing system 1212 can further include other removable/non-removable, volatile/non-volatile computer system storage media. By way of example only, storage system 1234 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media could be provided. In such instances, each can be connected to bus 1218 by one or more data media interfaces. As described below, memory 1223 can include at least one program product having a set (e.g., at least one) of program modules or code that are configured to carry out the functions of embodiments of the invention.

Program/utility 1240, having a set (at least one) of program modules 1242, can be stored in memory 1232 by way of example, and not limitation, as well as an operating system, one or more application programs, other program modules, and program data. Each of the operating system, one or more application programs, other program modules, and program data or some combination thereof, can include an implementation of a networking environment. Program modules 1242 generally carry out the functions and/or methodologies of embodiments of the invention as described herein. Alternatively, a UV light control facility, module, logic, etc., 1201 can be provided within computing environment 1212, as disclosed herein.

Computing system 1212 can also communicate with one or more external devices 1214 such as a keyboard, a pointing device, a display 1224, etc.; one or more devices that enable a user to interact with computing system 1212; and/or any devices (e.g., network card, modem, etc.) that enable computing system 1212 to communicate with one or more other computing devices. Such communication can occur via Input/Output (I/O) interfaces 1222. Still yet, computing system 1212 can communicate with one or more networks such as a local area network (LAN), a general wide area network (WAN), and/or a public network (e.g., the Internet) via network adapter 1220. As depicted, network adapter 1220 communicates with the other components of computing system, 1212, via bus 1218. It should be understood that although not shown, other hardware and/or software components could be used in conjunction with computing system 1212. Examples, include, but are not limited to: microcode, device drivers, redundant processing units, external disk drive arrays, RAID systems, tape drives, and data archival storage systems, etc.

The descriptions of the various embodiments of the present invention have been presented for purposes of illustration, but are not intended to be exhaustive or limited to the embodiments disclosed. Many modifications and variations will be apparent to those of ordinary skills in the art without departing from the scope and spirit of the described embodiments. The terminology used herein was chosen to best explain the principles of the embodiments, the practical application or technical improvement over technologies found in the marketplace, or to enable others of ordinary skills in the art to understand the embodiments disclosed herein.

The present invention may be a system, a method, and/or a computer program product at any possible technical detail level of integration. The computer program product can include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In addition to the above, one or more aspects may be provided, offered, deployed, managed, serviced, etc. by a service provider who offers management of customer environments. For instance, the service provider can create, maintain, support, etc. computer code and/or a computer infrastructure that performs one or more aspects for one or more customers. In return, the service provider may receive payment from the customer under a subscription and/or fee agreement, as examples. Additionally or alternatively, the service provider may receive payment from the sale of advertising content to one or more third parties.

In one aspect, an application may be deployed for performing one or more embodiments. As one example, the deploying of an application comprises providing computer infrastructure operable to perform one or more embodiments.

As a further aspect, a computing infrastructure may be deployed comprising integrating computer readable code into a computing system, in which the code in combination with the computing system is capable of performing one or more embodiments.

As yet a further aspect, a process for integrating computing infrastructure comprising integrating computer readable code into a computer system may be provided. The computer system comprises a computer readable medium, in which the computer medium comprises one or more embodiments. The code in combination with the computer system is capable of performing one or more embodiments.

Although various embodiments are described above, these are only examples. For example, computing environments of other architectures can be used to incorporate and use one or more embodiments. Further, different instructions, instruction formats, instruction fields and/or instruction values may be used. Many variations are possible.

Further, other types of computing environments can benefit and be used. As an example, a data processing system suitable for storing and/or executing program code is usable that includes at least two processors coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. An apparatus to facilitate cooling one or more electronic components, the apparatus comprising:
    a coolant-cooled heat sink through which coolant passes to facilitate cooling the coolant-cooled heat sink, the coolant-cooled heat sink including a base surface coupled to the one or more electronic components to facilitate cooling the one or more electronic components; and
    an ultra-violet (UV) light assembly associated with the coolant-cooled heat sink to direct UV light towards an interior surface of the coolant-cooled heat sink across which the coolant passes, to inhibit bacterial growth on the interior surface of the coolant-cooled heat sink.

2. The apparatus of claim 1, wherein the coolant-cooled heat sink includes a coolant-carrying compartment with a plurality of thermally-conductive fins disposed within the coolant-carrying compartment, and wherein the interior surface comprises one or more surfaces of the plurality of thermally-conductive fins disposed within the coolant-carrying compartment of the coolant-cooled heat sink.

3. The apparatus of claim 2, wherein the UV light assembly further comprises a UV light source to provide the UV light, and a control, the control being operatively coupled to control power to the UV light source, where a power level is set, at least in part, based on UV light intensity feedback received from a UV light sensor associated with the UV light source, the control powering the UV light source to produce the UV light for directing towards the interior surface of the coolant-cooled heat sink.

4. The apparatus of claim 2, wherein the ultra-violet (UV) light assembly comprises:
    a UV light source to provide the UV light; and
    a lens coupled to the coolant-cooled heat sink and operatively positioned relative to the UV light source to direct the UV light towards the interior surface of the coolant-cooled heat sink.

5. The apparatus of claim 4, wherein the lens is a collimating lens to direct collimated UV light towards the interior surface of the coolant-cooled heat sink.

6. The apparatus of claim 4, wherein the coolant passes through the thermally-conductive fins disposed within the coolant-carrying compartment from a coolant inlet side of the thermally-conductive fins to a coolant outlet side of the thermally-conductive fins, and wherein the lens is disposed to direct the UV light towards the coolant inlet side of the thermally-conductive fins.

7. The apparatus of claim 6, wherein the UV light source comprises a first UV light source, and the lens comprises a first lens, and wherein the ultra-violet light assembly further comprises a second UV light source and a second lens, the second UV light source and the second lens being located to operatively direct UV light towards the coolant outlet side of the thermally-conductive fins disposed within the coolant-carrying compartment of the coolant-cooled heat sink.

8. The apparatus of claim 2, wherein the ultra-violet (UV) light assembly further comprises:
    a UV light source to provide the UV light; and
    multiple UV light guides for directing the UV light towards the interior surface of the coolant-cooled heat sink, the multiple UV light guides extending into the coolant-cooled heat sink.

9. The apparatus of claim 8, further comprising a UV lens at an end of a UV light guide of the multiple UV light guides to facilitate directing the UV light towards the interior surface of the coolant-cooled heat sink.

10. An apparatus comprising:
    a coolant-cooled heat sink through which coolant passes to facilitate cooling the coolant-cooled heat sink;
    an ultra-violet (UV) light assembly associated with the coolant-cooled heat sink for directing UV light towards an interior surface of the coolant-cooled heat sink across which the coolant passes, the UV light inhibiting bacterial growth at the interior surface of the coolant-cooled heat sink; and
    wherein the coolant comprises an anti-corrosion material, and the UV light assembly comprises a control, a dosage of the UV light directed towards the interior surface being controlled by the control of the UV light assembly to maintain the anti-corrosion material in the coolant above a set level for a specified operational lifetime.

11. An apparatus comprising:
    multiple coolant-cooled heat sinks through which coolant passes to facilitate cooling the multiple coolant-cooled heat sinks; and
    an ultra-violet (UV) light assembly associated with the multiple coolant-cooled heat sinks for directing UV light towards respective interior surfaces of the multiple coolant-cooled heat sinks across which the coolant passes, the UV light inhibiting bacterial growth at the respective interior surfaces of the multiple coolant-cooled heat sinks.

12. The apparatus of claim 11, wherein each coolant-cooled heat sink of the multiple coolant-cooled heat sinks includes a coolant-carrying compartment with a plurality of thermally-conductive fins disposed within the coolant-carrying compartment, and wherein each interior surface comprises one or more surfaces of the plurality of thermally-conductive fins disposed within the coolant-carrying compartment of the respective coolant-cooled heat sink.

13. The apparatus of claim 12, wherein the coolant comprises an anti-corrosion material, and the UV light assembly comprises a control, a dosage of the UV light directed towards the respective interior surfaces being controlled by the control to maintain the anti-corrosion material in the coolant above a set level for a specified operational lifetime.

14. The apparatus of claim 12, wherein the ultra-violet (UV) light assembly comprises:
    at least one UV light source to provide the UV light; and
    multiple lenses, each lens being coupled to a respective coolant-cooled heat sink of the multiple coolant-cooled heat sinks, and being positioned relative to the UV light source to direct the UV light towards the respective interior surface of the coolant-cooled heat sink.

15. The apparatus of claim, 12, wherein the ultra-violet (UV) light assembly comprises:
    a UV light source to provide the UV light; and
    multiple UV light guides coupled to one coolant-cooled heat sink of the multiple coolant-cooled heat sinks, and being positioned relative to the UV light source to direct the UV light towards the respective interior surface of the one coolant-cooled heat sink.

16. The apparatus of claim 15, wherein the multiple UV light guides comprise a first set of UV light guides, and wherein the UV light assembly further comprises a second set of UV light guides, the second set of UV light guides being coupled to another coolant-cooled heat sink of the multiple coolant-cooled heat sinks and being positioned relative to the UV light source to direct the UV light towards the respective interior surface of the other coolant-cooled heat sink, wherein the UV light source provides the UV light for at least two coolant-cooled heat sinks of the multiple coolant-cooled heat sinks.

17. The apparatus of claim 11, wherein the ultra-violet (UV) light assembly further comprises:
    a UV light source to provide the UV light; and
    a control operatively coupled to control power to the UV light source, where a power level is set by the control, at least in part, via UV light intensity feedback received from a UV light sensor associated with the UV light source, the control powering the UV light source to provide the UV light for directing towards the respective interior surfaces of the multiple coolant-cooled heat sinks.

* * * * *